US011939360B2

(12) United States Patent
Yang et al.

(10) Patent No.: US 11,939,360 B2
(45) Date of Patent: Mar. 26, 2024

(54) **PHARMACEUTICAL COMPOSITION FOR PREVENTING OR TREATING INFLAMMATORY DISEASES INCLUDING *TOXOPLASMA GONDII* GRA9 PROTEIN OR GENE ENCODING THE PROTEIN AS ACTIVE INGREDIENT**

(71) Applicant: INDUSTRY-UNIVERSITY COOPERATION FOUNDATION HANYANG UNIVERSITY ERICA CAMPUS, Gyeonggi-do (KR)

(72) Inventors: Chul-Su Yang, Gyeonggi-do (KR); Jae-Sung Kim, Gyeonggi-do (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 0 days.

(21) Appl. No.: 17/682,544

(22) Filed: Feb. 28, 2022

(65) Prior Publication Data
US 2022/0306707 A1    Sep. 29, 2022

(30) Foreign Application Priority Data
Mar. 16, 2021    (KR) ........................ 10-2021-0033920

(51) Int. Cl.
*A61P 31/04* (2006.01)
*A23L 33/00* (2016.01)
*A23L 33/195* (2016.01)
*A61K 38/00* (2006.01)
*A61P 37/06* (2006.01)
*C07K 14/45* (2006.01)

(52) U.S. Cl.
CPC ............ *C07K 14/45* (2013.01); *A23L 33/195* (2016.08); *A23L 33/40* (2016.08); *A61P 31/04* (2018.01); *A61P 37/06* (2018.01); *A23V 2002/00* (2013.01); *A61K 38/00* (2013.01)

(58) Field of Classification Search
None
See application file for complete search history.

(56) References Cited

PUBLICATIONS

MedLinePlus, Is gene therapy safe? 1-2, 2022 (Year: 2022).*
Danielski et al. "Toxoplasma gondii GRA9 Regulates the Activation of NLRP3 Inflammasome to Exert Anti-Septic Effects in Mice" published on Nov. 10, 2020, International Journal of Molecular Sciences, 16 Pages.
Danielski et al. "The NLRP3 Inflammasome and Its Role in sepsis Development" Springer Science & Business Media, LLC, Published online: Nov. 18, 2019, 8 Pages.

* cited by examiner

*Primary Examiner* — Thomas S Heard
(74) *Attorney, Agent, or Firm* — Armstrong Teasdale LLP

(57) ABSTRACT

The present invention relates to a pharmaceutical composition and a health functional food composition for preventing, alleviating or treating inflammatory diseases, including *Toxoplasma gondii* GRA9 protein or a gene encoding the protein as an active ingredient. The present inventors have identified the C-terminal region essential for the NLRP3-mediated mechanism of action and function of *Toxoplasma gondii* GRA9 in macrophages, which are host immune cells and confirmed the substantial anti-inflammatory and anti-bacterial effects and the antiseptic effect in vivo. Accordingly, *Toxoplasma gondii* GRA9 protein or a gene encoding the protein is expected to be usefully utilized in the field of prevention or treatment of inflammatory diseases caused by an abnormal NLRP3-mediated inflammatory response, including sepsis.

6 Claims, 31 Drawing Sheets
Specification includes a Sequence Listing.

PHARMACEUTICAL COMPOSITION FOR PREVENTING OR TREATING INFLAMMATORY DISEASES INCLUDING *TOXOPLASMA GONDII* GRA9 PROTEIN OR GENE ENCODING THE PROTEIN AS ACTIVE INGREDIENT

CROSS-REFERENCE TO RELATED APPLICATION

This application claims the benefit of Korean Patent Application No. 10-2021-0033920 filed on Mar. 16, 2021, in the Korean Intellectual Property Office, the entire disclosure of which is incorporated herein by reference for all purposes.

REFERENCE TO AN ELECTRONIC SEQUENCE LISTING

The contents of the electronic sequence listing (38009-17_ST25.txt; Size: 6,458 bytes; and Date of Creation: Mar. 17, 2022) is herein incorporated by reference in its entirety.

BACKGROUND

1. Field of the Invention

The present invention relates to a pharmaceutical composition and a health functional food composition for preventing, alleviating or treating inflammatory diseases, including *Toxoplasma gondii* GRA9 protein or a gene encoding the protein as an active ingredient.

2. Description of the Related Art

*Toxoplasma gondii* is an intracellular parasite that is one of the most widespread species worldwide and causes Toxoplasmosis. *Toxoplasma gondii* has 23 excretory/secretory dense granule antigens (GRAs). Many studies indicate that GRA protein interferes with the host cell transcription system to actively regulate host gene expression. GRA9, which is one of the GRAs, is known to be essential for the tachyzoite and bradyzoite stages, which are the stages in which the host is infected with *Toxoplasma gondii*. GRA9 has also been proposed as a vaccine candidate against Toxoplasmosis caused by *Toxoplasma gondii* infection. However, the role of *Toxoplasma gondii* GRA9 in the host and how it regulates host immune system-related factors are still not well understood.

The NLR family pyrin domain containing 3 (NLRP3) constitutes a leucine-rich repeat-containing receptor and recognizes pathogen-associated molecular patterns (PAMPs) and damage-associated molecular patterns (PAMPs) derived from pathogens, damaged tissues and cells. In inflammation, NLRP3 assembles with apoptotic speck-containing protein (ASC), which is a connective protein, and pro-caspase-1, which is an effector protein, to construct the NLRP3 inflammasome. NLRP3 inflammasome induces maturation of interleukin-1β (IL-1β) and interleukin-18 (IL-18) for secretion of inflammatory cytokines and induces proximal caspase-1 autoprotein degradation. In addition, activated caspase-1 induces cleavage of gasdermin D, leading to a pro-inflammatory programmed cell death called pyroptosis. NLRP3 signaling is known to be an important signaling pathway in the innate immune system and inflammatory processes. In addition, various inflammatory diseases, including Parkinson's disease, Alzheimer's disease, inflammatory bowel disease, and atherosclerosis, have been related to the NLRP3 inflammasome. However, the mechanism of *Toxoplasma gondii* GRA9 for the activation and role of NLRP3 inflammasome has not been studied yet.

Meanwhile, sepsis is defined as life-threatening organ dysfunction caused by an uncontrolled host response to infection. Sepsis is regarded as one of the major public health problems every year due to its high incidence and mortality worldwide. The early stages of sepsis are associated with hyperinflammation with increased release of inflammatory cytokines and chemokines from immune cells called "systemic inflammatory response syndrome." For the treatment of sepsis, appropriate antibiotics for bacterial infection control are required, and antibiotics are selected according to the type of bacteria and the condition of the patient. Modulating the host's immune response is also a therapeutic strategy for sepsis. Many pattern recognition receptors are known to be involved in the inflammatory activation of sepsis. Some studies have reported that NLRP3 is a key factor involved in the inflammation of sepsis, and activation of the NLRP3 inflammasome during sepsis is associated with mitochondrial dysfunction and organ damage.

Accordingly, the present inventors demonstrated that GRA9 of *Toxoplasma gondii* interacts with NLRP3 and inhibits ASC binding to NLRP3 in mitochondria to reduce NLRP3 inflammasome formation. Furthermore, the present invention was completed by confirming that the C-terminus of GRA9 is essential for interaction with NLRP3, improves anti-inflammatory and antibacterial effects through polarization of macrophages from M1 to M2, and exhibits antiseptic effect in vivo.

SUMMARY

Accordingly, an object of the present invention is to provide a pharmaceutical composition for preventing or treating inflammatory diseases, the composition including *Toxoplasma gondii* GRA9 protein or a gene encoding the protein as an active ingredient.

Another object of the present invention is to provide a health functional food composition for preventing or alleviating inflammatory diseases, the composition including *Toxoplasma gondii* GRA9 protein or a gene encoding the protein as an active ingredient.

However, the technical problem to be achieved by the present invention is not limited to the above-mentioned problems, and other problems not mentioned are clearly understood by those skilled in the art from the following description.

In order to achieve the object of the present invention as described above, the present invention provides a pharmaceutical composition for preventing or treating inflammatory diseases, including *Toxoplasma gondii* GRA9 protein or a gene encoding the protein as an active ingredient.

Further, the present invention provides a use of the composition for alleviating, preventing, and/or treating an inflammatory disease, and the composition may be mixed with an appropriate carrier and provided as a pharmaceutical composition for preventing or treating an inflammatory disease and provided as a health functional food composition for preventing or alleviating the disease.

Further, the present invention provides a method for preventing or treating an inflammatory disease, the method including administering the composition to a subject.

Further, the present invention provides the use of the composition for the manufacture of a medicament for preventing or treating inflammatory diseases.

In one embodiment of the present invention, the inflammatory disease may be sepsis.

In another embodiment of the present invention, the GRA9 protein may include or consist of the amino acid sequence represented by SEQ ID NO: 1.

In another embodiment of the present invention, the GRA9 protein may include or consist of a C-terminal region corresponding to positions 195 to 288 in the amino acid sequence of the GRA9 protein represented by SEQ ID NO: 1.

In another embodiment of the present invention, the GRA9 protein may necessarily include glutamine (Q) at position 200 in the C-terminal region.

In another embodiment of the present invention, the GRA9 protein may interact with the NLR family pyrin domain containing 3 (NLRP3) in the mitochondria of macrophages to inhibit the formation of NLRP3 inflammasome.

In another embodiment of the present invention, the composition may reduce NLRP3-mediated inflammation.

In another embodiment of the present invention, the composition may enhance anti-inflammatory and antibacterial effects through polarization and phagocytosis from M1 to M2 macrophages.

In another embodiment of the present invention, the subject may be a mammal, particularly a human, having a high probability of developing an inflammatory disease due to the onset of an inflammatory disease or an infection of a pathogen.

The present inventors have identified the C-terminal region essential for the NLRP3-mediated mechanism of action and function of *Toxoplasma gondii* GRA9 in macrophages, which are host immune cells and confirmed the substantial anti-inflammatory and antibacterial effects and the antiseptic effect in vivo. Accordingly, *Toxoplasma gondii* GRA9 protein or a gene encoding the protein is expected to be usefully utilized in the field of prevention or treatment of inflammatory diseases caused by an abnormal NLRP3-mediated inflammatory response, including sepsis.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIGS. 1A-1B show the results confirming that GRA9 binds to NLRP3 in which FIG. 1A shows the result of mass spectrometry on a human monocyte THP-1 cell lysate expressing a vector or GRA9, and FIG. 1B shows the results of immunoprecipitation (IP) and immunoblotting for each treatment time by treating and stimulating a vector or GRA9 expression THP-1 cells with LPS (100 ng/ml) and treating with ATP or nigericin;

FIGS. 2A-2E show the results confirming that GRA9 inhibits the binding of NLRP3 and ASC in mitochondria and interacts with NLRP3 in which FIG. 2A shows the results of analyzing the expression levels of GRA9, NLRP3 and ASC proteins by performing immunoblotting on each cell fraction (cytosol, endoplasmic reticulum (ER), mitochondrial associated membrane (MAM) and mitochondria (mito)) of vector or GRA9 expressing THP-1 cells activated with LPS stimulation and ATP, FIG. 2B shows the results of observing each THP-1 cell treated with LPS and ATP in the same manner as FIG. 2A, which was immunolabeled with αFlag (Alexa 568), MitotrackerDeep Green and DAPI, respectively, under a confocal microscope, FIG. 2C shows the results of analyzing the interaction of NLRP3 with GRA9 and ASC in each fraction by immunoprecipitation using the cytoplasmic fraction (cytosol) and mitochondrial fraction (mito) of each THP-1 cell treated with LPS and ATP, FIG. 2D shows an image observed with a confocal microscope of each THP-1 cell treated with LPS and ATP, which was immunolabelled with αFlag-GRA9 (Alexa 568), αNLRP3 (Alexa 488) and DAPI, respectively, and three-dimensional analysis results thereof, and FIG. 2E shows the results of immunoprecipitation with Flag or AU1 on 293T cells transfected with V5-GRA9, Flag-NLRP3 and AU1-ASC;

FIGS. 3A-3C show the results confirming that the C-terminus of GRA9 binds to NLRP3 to attenuate the induction of NLRP3 inflammasome in which FIG. 3A shows a schematic diagram of the structures of GRA9 and NLRP3 proteins (top); and the results of GST pulldown and immunoprecipitation, respectively, on 293T cells transfected with Flag-NLRP3 and GST-GRA9 wild-type (WT) or its truncated mutants (N, C, $C^{Q200L}$) or with V5-GRA9 and Flag-NLRP3 wild-type (WT) or its truncated mutants (PYD, NACHD, LRR) (bottom), FIG. 3B shows the results of analyzing levels of IL-1β p17, IL-18 p18 and Casp 1 p10 proteins in the truncated form in the culture supernatant (SN) by immunoblotting on vector, GRA9C or GRA9C$^{Q200L}$ expressing THP-1 cells stimulated with LPS and treated with ATP or DSS for 1 hour or 18 hours, and FIG. 3C shows the results of measuring the levels of IL-1β, IL-18, TNF-α, IL-6 and IL-12p40 cytokines in each of the THP-1 cells by ELISA (***P<0.001);

FIGS. 4A-4F show the results confirming that rGRA9C interacts with NLRP3 to reduce the activation of NLRP3 inflammation under physiological conditions in which FIG. 4A shows the results confirmed by immunoblotting for Coomassie blue staining (left) and αHis (right) of the 6×His-GRA9C and rGRA9C$^{Q200L}$ proteins expressed and purified in bacteria, FIG. 4B shows the results of measuring cell viability by MTT assay to verify cytotoxicity for bone marrow-derived macrophages (BMDMs) isolated from mice, which were treated with rVehicle, rGRA9C or rGRA9C$^{Q200L}$, FIG. 4C shows an image observed with a confocal microscope on rVehicle, rGRA9C, or rGRA9C$^{Q200L}$-treated BMDMs immunolabelled with αFlag-rGRA9C (Alexa 586), αNLRP3 (Alexa 488) and DAPI, and a three-dimensional analysis results thereof, FIG. 4D is results of re-verification of ASC binding inhibition and interaction with NLRP3 by performing immunoprecipitation after treating LPS and ATP-treated BMDMs with rVehicle, rGRA9C or rGRA9C$^{Q200L}$ at various concentrations, FIG. 4E shows the results of confirming the levels of IL-1β p17, IL-18 p18 and Casp1 p10 proteins through immunoblotting in the culture supernatant of cells treated in the same manner as in FIG. 4D, and FIG. 4F shows the results of analyzing the IL-1β and IL-18 levels through ELISA for LPS-stimulated BMDMs treated with ATP or DSS, which were treated with rVehicle, rGRA9C or rGRA9C$^{Q200L}$ (***p<0.001);

FIGS. 5A-5E show the results confirming that rGRA9C improves anti-inflammatory and antibacterial effects through polarization from M1 to M2 in which FIG. 5A shows the results of measuring the levels of TNF-α, IL-6, IL-10 and TGF-β by ELISA for LPS-stimulated BMDMs treated with rGRA9C at various concentrations (0.1, 1, or 10 μg/ml), FIG. 5B is the result of analyzing the expression levels of M1 macrophage markers (CD86 and iNOS) and M2 macrophage markers (CD163 and Arg1) through quantitative real-time PCR after treatment with rVehicle, rGRA9C or rGRA9C$^{Q200L}$ in LPS-stimulated BMDMs, FIG. 5C shows the results of analyzing the expression levels of SR-A, FcR, TLR4, TLR1, TLR2 and TLR6 through FACS analysis in BMDMs treated with rVehicle, rGRA9C or rGRA9C$^{Q200L}$, FIG. 5D shows the result of comparative analysis of the antibacterial effect after infecting BMDMs with *Escherichia coli* (*E. coli*) (MOI=50) or *Pseudomonas aeruginosa* (*P. aeruginosa*) (MOI=20) for 4 hours, respectively, and treatment with rVehicle, rGRA9C or rGRA9C$^{Q200L}$ for 12 hours, and FIG. 5E shows the result of analyzing the antibacterial effect according to each treatment concentration of rGRA9C after infecting BMDMs with *E. coli* or *P. aeruginosa* (*P<0.05; P<0.01; *P<0.001);

FIGS. 6A-6F show the results confirming that rGRA9C protects mice from septic shock induced by CLP, in which FIG. 6A shows an experimental schematic (top) of a mouse model of CLP sepsis administered with the indicated concentrations of rVehicle, rGRA9 or rGRA9C$^{Q200L}$ and the results shown by measuring the survival rate of each mouse group (n=25 per group, bottom), FIGS. 6B and 6C show, after administration of rVehicle, rGRA9C or rGRA9C$^{Q200L}$ to CLP sepsis mice (n=10 per group), the results of measuring the level of cytokines in the serum from 18 hours (FIG. 6B), and the results of measuring the number of bacteria in the blood and peritoneal fluid (FIG. 6C), FIG. 6D shows the results of hematoxylin and eosin (H&E) staining of tissue sections of the lung, liver and spleen removed from each group of mice as described above (top), and the results of the evaluation with histopathological scores (bottom), and FIGS. 6E and 6F show the results of immunoprecipitation on mouse-derived splenocytes of the same groups as described above (FIG. 6E) and the results of measuring expression levels of M1 (CD86 and iNOS) and M2 (CD163 or Arg1) macrophage markers (FIG. 6F) (*P<0.05, P<0.01; *P<0.001); and FIGS. 7A-7D show the results confirming that rGRA9C protects mice from septic shock induced by a bacterial infection in which FIG. 7A shows an experimental schematic diagram (top) of *E. coli* or *P. aeruginosa*-infected sepsis mouse model, which was administered with rVehicle, rGRA9 or rGRA9C$^{Q200L}$ and the results of measuring the survival rate of each mouse group (n=10 per group, bottom), FIG. 7B shows the results of measuring OD$_{600}$ every 6 hours while culturing *E. coli* or *P. aeruginosa* with rVector, rGRA9 or rGRA9C$^{Q200L}$ (50 μg/ml) in LB medium at 37° C. for 36 hours, FIG. 7C shows the results of measuring the number of bacteria in the blood and peritoneal fluid 24 hours and 2 days, respectively, after administrating sepsis mice infected with *E. coli* or *P. aeruginosa* with rVehicle, rGRA9C or rGRA9C$^{Q200L}$ (n=10 per group), and FIG. 7D shows the results of measuring the expression levels of M1 (CD86 and iNOS) and M2 (CD163 or Arg1) macrophage markers in mouse-derived splenocytes of each group (*P<0.05; P<0.01; *P<0.001).

DETAILED DESCRIPTION

Figure 1A:
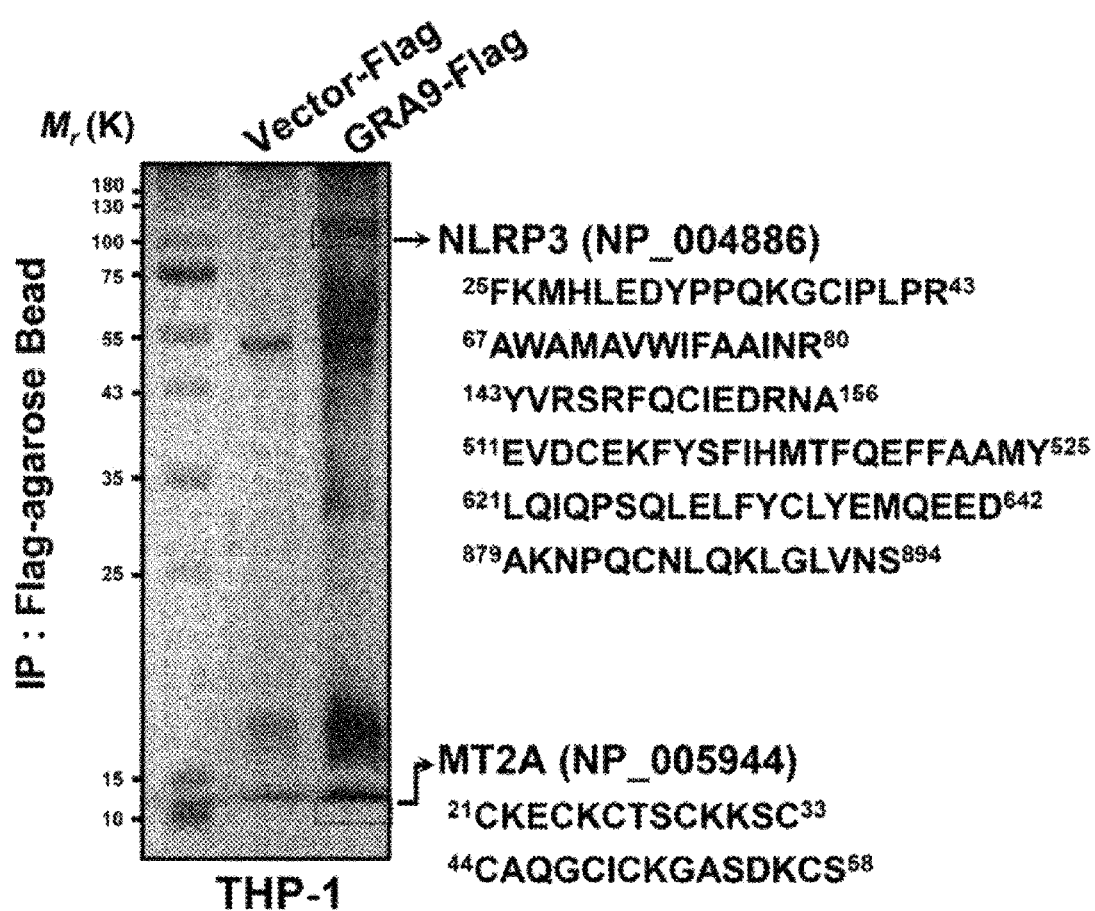

The present invention relates to the use of *Toxoplasma gondii*-derived GRA9 for the prevention or treatment of inflammatory diseases, confirms the anti-inflammatory and antibacterial effects of GRA9 and specifically the antiseptic effect, and elucidates the NLRP3-mediated mechanism of GRA9 in macrophages, which are host immune cells to complete the present invention.

Accordingly, the present invention provides a pharmaceutical composition for preventing or treating inflammatory diseases, the composition including the *Toxoplasma gondii* (*T. gondii*) GRA9 protein or a gene encoding the protein as an active ingredient.

As used herein, the term "prevention" refers to any action that suppresses or delays the onset of an inflammatory disease by administration of the pharmaceutical composition according to the present invention.

As used herein, the term "treatment" refers to any action in which symptoms for inflammatory diseases are alleviated or beneficially changed by administration of the pharmaceutical composition according to the present invention.

The present inventors identified the mechanism of action that *Toxoplasma gondii* GRA9 inhibits the binding of NLRP3 and ASC in the mitochondria of macrophages in the host and interacts with NLRP3 to inhibit NLRP3 inflammasome formation and inflammatory response in the host through specific examples and confirmed that anti-inflammatory and antibacterial effects were improved through the polarization of phagocytes from M1 to M2, and further confirmed the antiseptic effect in CLP and bacterial sepsis in vivo models.

An "inflammatory disease," which is a disease targeted by the present invention, is a disease whose main lesion is inflammation and may be induced by causes such as infection, allergy/hypersensitivity reaction, autoimmunity, or damage/exposure to harmful substances. In the present invention, the inflammatory disease preferably means an inflammatory disease in which NLRP3 is a major mediator of the inflammatory response, more preferably sepsis, but is not limited thereto.

Sepsis refers to a systemic inflammatory reaction syndrome caused when blood is infected with bacteria invading the human body and the infected subject may die within a short time. There are a wide variety of causative bacteria including Streptococci, *Staphylococcus, Escherichia coli, Pneumococcus, Pseudomonas aeruginosa,* and fungi. It can be infected by introducing the causative bacteria of purulent diseases in the human body into the blood, and can also be infected through food intake, such as *Vibrio* sepsis. Even if blood is not directly infected with bacteria, symptoms may appear due to inflammatory substances from an infectious source in one part of the body. It is known that although NLRP3 inflammasome induces an inflammatory response essential to protect the human body from external microorganisms, excessive activation can cause organ damage and, in severe cases, cause sepsis, an excessive systemic immune-inflammatory response.

In the present invention, the *Toxoplasma gondii* GRA9 protein may include or consist of the amino acid sequence represented by SEQ ID NO: 1, and the gene encoding the protein may include or consist of the nucleotide sequence represented by SEQ ID NO: 2. At this time, it may include an amino acid sequence and a nucleotide sequence having 70% or more, preferably 80% or more, more preferably 90% or more, most preferably 95% or more sequence homology with the amino acid sequence represented by SEQ ID NO: 1 and the nucleotide sequence represented by SEQ ID NO: 2.

In the present invention, the GRA9 protein may preferably be or include a C-terminal region corresponding to positions 195 to 288 in the amino acid sequence represented by SEQ ID NO: 1, in which it may necessarily include glutamine (Q) at position 200 in the C-terminal region.

The pharmaceutical composition according to the present invention includes a GRA9 protein or a gene encoding the protein as an active ingredient and may further include a pharmaceutically acceptable carrier. The pharmaceutically acceptable carrier is commonly used in formulation and includes, but is not limited to, saline, sterile water, Ringer's solution, buffered saline, cyclodextrin, dextrose solution, maltodextrin solution, glycerol, ethanol, liposome, and the like. If necessary, it may further include other conventional additives such as antioxidants and buffers. In addition, it may be further added with a diluent, dispersant, surfactant, binder, lubricant, etc. to be formulated into an injectable formulation such as an aqueous solution, suspension, emulsion, etc., pills, capsules, granules or tablets. Regarding suitable pharmaceutically acceptable carriers and formulations, formulations may be preferably made according to each component using the method disclosed in Remington's literature. The pharmaceutical composition of the present invention is not particularly limited in formulation, but may be formulated as an injection, inhalant, or external preparation for the skin.

The pharmaceutical composition of the present invention may be administered orally or parenterally (e.g., intravenously, subcutaneously, intraperitoneally or topically) according to a desired method, but preferably may be administered orally. The dosage varies depending on the patient's condition and weight, the degree of disease, drug form, administration route and time, but it may be appropriately selected by those skilled in the art.

The pharmaceutical composition of the present invention is administered in a pharmaceutically effective amount. In the present invention, "pharmaceutically effective amount" means an amount sufficient to treat or diagnose a disease at a reasonable benefit/risk ratio applicable to medical treatment or diagnosis, and the effective dose level may be determined by factors including the patient's disease type, severity, and drug activity, sensitivity to drugs, administration time, administration route and excretion rate, treatment period, concurrent drugs, and other factors well known in the medical field. The pharmaceutical composition according to the present invention may be administered as an individual therapeutic agent or may be administered in combination with other therapeutic agents. It may be administered sequentially or simultaneously with conventional therapeutic agents and may be administered single or multiple. In consideration of all of the above factors, it is important to administer an amount that can obtain the maximum effect with a minimum amount without side effects, which can be easily determined by those skilled in the art.

In particular, the effective amount of the pharmaceutical composition of the present invention may vary depending on the patient's age, sex, condition, weight, absorption of the active ingredient into the body, inactivation rate and excretion rate, disease type, and drugs used in combination, generally 0.001 to 150 mg, preferably 0.01 to 100 mg per 1 kg of body weight daily or every other day, or divided into 1 to 3 times a day. However, since the dosage may be increased or decreased according to the administration route, the severity of obesity, sex, weight, age, etc., the dosage is not intended to limit the scope of the present invention in any manner.

As another aspect of the present invention, the present invention provides a health functional food composition for preventing or alleviating inflammatory diseases, the composition including the *Toxoplasma gondii* (*T. gondii*) GRA9 protein or a gene encoding the protein as an active ingredient.

As used herein, the term "alleviation" refers to any action that at least reduces a parameter related to the condition being treated, for example, the severity of symptoms. In this case, the health functional food composition may be used simultaneously with or independently from a drug for treatment before or after the onset of the disease in order to prevent or alleviate an inflammatory disease.

As used herein, the term "health functional food composition" is formulated into one selected from the group consisting of tablets, pills, grains, granules, powders, capsules and liquid formulations by including one or more of carriers, diluents, excipients and additives. Foods that may be added to the extract of the present invention include various foods, powders, granules, tablets, capsules, syrups, beverages, gums, tea, vitamin complexes, and health functional foods. Additives that may be further included in the present invention may include at least one component selected from the group consisting of natural carbohydrates, flavoring agents, nutrients, vitamins, minerals (electrolytes), flavoring agents (synthetic flavoring agents, natural flavoring agents, etc.), coloring agents, fillers, pectic acid and its salts, alginic acid and its salts, organic acids, protective colloidal thickeners, pH adjusters, stabilizers, preservatives, antioxidants, glycerin, alcohols, carbonation agents and pulp. Examples of the above-mentioned natural carbohydrates include monosaccharides such as glucose and fructose; disaccharides such as maltose and sucrose; and polysaccharides such as conventional sugars such as dextrin and cyclodextrin, and sugar alcohols such as xylitol, sorbitol, and erythritol. As the flavoring agent, natural flavoring agents (Thaumatin, *stevia* extract (for example, rebaudioside A, glycyrrhizin, etc.) and synthetic flavoring agents (saccharin, aspartame, etc.) may be advantageously used. In addition, the composition according to the present invention may include various nutrients, vitamins, minerals (electrolytes), flavoring agents such as synthetic flavoring agents and natural flavoring agents, coloring agents and thickening agents, pectic acid and its salts, alginic acid and its salts, organic acids, protective colloidal thickeners, pH adjusters, stabilizers, preservatives, antioxidants, glycerin, alcohols, carbonation agents used for carbonated drink. In addition, the composition according to the present invention may contain pulp for the production of natural fruit juices and vegetable beverages. These components may be used independently or in combination. Specific examples of the carrier, excipient, diluent and additive include, but are not limited to, preferably at least one selected from the group consisting of lactose, dextrose, sucrose, sorbitol, mannitol, erythritol, starch, acacia gum, calcium phosphate, alginate, gelatin, calcium phosphate, calcium silicate, microcrystalline cellulose, polyvinyl pyrrolidone, cellulose, methylcellulose, water, sugar syrup, methylhydroxybenzoate, propylhydroxybenzoate, talc, magnesium stearate and mineral oil.

Hereinafter, preferred examples are provided to help the understanding of the present invention. However, the following examples are only provided for easier understanding of the present invention, and the contents of the present invention are not limited by the following examples.

EXAMPLE

Example 1. Experimental Materials and Methods

1-1. Mice and Cell Culture

The wild-type C57BL/6 mice used in Examples of the present invention were purchased from Samtako Bio Korea (Gyeonggi-do, Korea). Primary bone marrow-derived macrophages (BMDM) isolated from 6-week-old C57BL/6 mice were cultured in DMEM in the presence of M-CSF (R & D Systems, 416-ML) for 3 to 5 days according to a known method. HEK293T (ATCC-11268; American Type Culture Collection) or THP-1 (ATCC-TIB-202) cells were cultured in RPMI1640 (Gibco) or DMEM containing 10% FBS (Gibco, NY, USA), sodium pyruvate, non-essential amino acids, penicillin G (100 IU/ml) and streptomycin (100 μg/ml). In addition, transient transfection was performed in 293T cells using calcium phosphate (Clontech, Mountain View, CA, USA) according to the manufacturer's protocol, and the THP-1 stable cell line was transfected with Lipofectamine 3000 (Invitrogen, Waltham, MA, USA), followed by a standard selection protocol using 400 to 800 μg/ml of G418.

1-2. Recombinant Protein

In order to obtain recombinant GRA9 (GenBank Accession No. XP 002367395.1) protein derived from *T. gondii* ME49 strain, GRA9C amino acid residues (195-288) and GRA9C$^{Q200L}$ with an N-terminal 6× His tag were cloned into combined with pRSFDuet-1 vector (Novagen, NJ, USA). Then, the expression of the protein was induced from *E. coli* expression strain BL21(DE3) pLysS according to the standard protocol recommended by the manufacturer, followed by recovery and purification. Next, the purified rGRA9 recombinant protein was dialyzed against a permeable cellulose membrane, and a test of lipopolysaccharide (LPS) contamination was performed by *Limulus* amebocyte lysate assay (BioWhittaker). It was confirmed that the rGRA9 and mutant proteins used in this Example were contained at a concentration of 20 pg/ml or less.

1-3. Reagents and Antibodies

LPS (L3024), ATP (A1852), nigericin (N7143) and DSS (D8906) were purchased from Sigma-Aldrich (St. Louis, MO, USA). Specific antibodies against Flag (D-8), GST (B-14), V5 (E10), NLRP3 (H-66), ASC (N-15), TXNIP (D-2), Tubulin (5F131), Calnexin (AF18), FACL4 (N-18), caspase-1 (14F468, M-20) and Actin (I-19) were purchased from Santa Cruz Biotechnology (Dallas, TX, USA). Specific antibodies against Calreticulin (D3E6) and IL-18 (D2F3B) were purchased from Cell Signaling Technology (Danvers, MA, USA). IL-1β (AF-401-NA) was purchased from R&D Systems, and NLRP3 (AG-20B-0014) was purchased from Adipogen (San Diego, CA, USA). Antibodies against COX IV (ab16056) and AU1 (ab3401) were also purchased from Abcam (Cambridge, UK).

1-4. Plasmid Construction

The known plasmids encoding the full-length NLRP3, ASC, and NLRP3 mutations were used. Further, plasmids encoding other regions of GRA9 (1-318, 18-171, 195-288, Q200L) were prepared by PCR amplification from the full-length GRA9 cDNA, followed by subcloning between BamHI and NotI restriction enzyme sites of the pEBG derivative encoding the N-terminal GST epitope tag. Transient and stable expression of all constructs in mammalian cells was achieved via the pEBG-GST mammalian fusion vector and the pEF-IRES-Puro expression vector. All constructs were sequenced using an ABI PRISM 377 automated DNA sequencer (Thermofisher, Waltham, MA, USA) to verify that they were 100% identical to the original sequence.

1-5. Enzyme-Linked Immunosorbent Assay

In order to detect TNF-α, IL-6, IL-1β, IL-18, IL-12p40, IL-10 and TGF-β, cytokine content was analyzed in cell culture and mouse serum using the BD OptEIA ELISA set (BD Pharmingen) according to the manufacturer's recommended protocol.

1-6. Sepsis Induced by CLP and Bacterial Count

Cecal ligation and puncture (CLP) was attempted using a 6-week-old C57BL/6 female mouse according to a known method. For this purpose, the mice were anesthetized with pentothal sodium (50 mg/kg, i.p.), and then the cecum was exposed through a small incision in the middle of the abdomen. The cecum was connected under the serosal septum, and the abdomen was closed by puncturing it twice through both sides using a 22 gauge needle. Thereafter, the survival rate was monitored daily for 10 days. Further, mice were intraperitoneally injected with PBS, analgesic (1.5 mg/kg nalbuphine; Sigma-Aldrich), and an antibiotic cocktail containing ceftriaxone (25 mg/kg; Sigma-Aldrich) and metronidazole (12.5 mg/kg; Sigma-Aldrich) in 100 μl PBS at 12 and 24 hours after initiation of CLP to resuscitate the mice. For experiments to isolate blood and organ samples, mice with exposed cecum but not ligated or perforated were used and marked with sham at the time of surgery.

Meanwhile, in order to measure the number of bacteria, blood was collected via cardiac puncture or peritoneal lavage from mice at designated times after CLP. After serial dilution of blood, 5 μl of each dilution was plated on a blood agar plate. After culturing at 37° C. for 24 hours, the number of bacteria was counted by counting the number of colony forming units per blood or total peritoneal lavage.

All animals were raised in a pathogen-free environment. All animal experiments were conducted after being reviewed and approved by the Animal Experimental Ethics Committee (protocol 2018-0086) of Hanyang University. Post-CLP analgesia, fluid support, and antibiotics were followed by international guidelines defined as 'minimum quality thresholds in preclinical sepsis studies' for the sepsis mouse model to improve the model's mediation relevance.

1-7. GST Pulldown, Immunoblotting and Immunoprecipitation Analysis

For GST pulldown, cells were harvested and lysed in NP-40 buffer supplemented with a complete protease inhibitor cocktail (Roche). After centrifugation, the supernatant was first removed with protein A/G beads at 4° C. for 2 hours. The previously removed lysate was mixed with a 50% slurry of glutathione-conjugated Sepharose beads (Amersham Biosciences) and cultured at 4° C. for 4 hours to induce a binding reaction. The precipitate was extensively washed with lysis buffer, and the protein bound to glutathione beads was boiled for 5 minutes and eluted with SDS loading buffer.

For immunoprecipitation, cells were harvested and then lysed in NP-40 buffer supplemented with a complete protease inhibitor cocktail (Roche). The supernatant was first removed with protein A/G agarose beads at 4° C. for 2 hours, and then whole cell lysates were used to perform immunoprecipitation with the indicated antibodies. In general, 1-4 μg of commercial antibody was added to 1 ml of cell lysate, and the mixture was cultured at 4° C. for 8 to 12 hours. Next, protein A/G agarose beads were added for 6 hours, and the immunoprecipitates were washed extensively with lysis buffer and then boiled for 5 minutes and eluted with SDS loading buffer.

For immunoblotting, polypeptides were separated by SDS-polyacrylamide gel electrophoresis (PAGE) and transferred to PVDF membrane (Bio-Rad). Immunodetection was performed with an antibody specific for each protein, and antibody binding was visualized by chemiluminescence (ECL; Millipore) and detected by a Vilber chemiluminescence analyzer (Fusion SL 3; Vilber Lourmat).

1-8. Histological Analysis

For immunohistochemistry of tissue sections, spleen, liver and lungs of mice were fixed in 10% formalin and embedded in paraffin. Then, paraffin sections were cut to a thickness of 4 and stained with hematoxylin and eosin (H&E). The histopathological score was set based on the number and distribution of inflammatory cells and the degree of inflammation in the tissue. Each organ compartment was scored independently by a professional pathologist without prior information about the treatment group, and each specimen was assigned a histological score ranging from 0 to 4.

1-9. Protein Purification and Mass Spectrometry

In order to identify GRAS binding proteins, THP-1 cells expressing Flag-GRAS or vector were harvested and dissolved with NP-40 buffer (50 mM HEPES, pH 7.4, 150 mM NaCl, 1 mM EDTA, 1% (v/v) NP40) supplemented with a complete protease inhibitor cocktail. After centrifugation, the supernatant was first removed with protein A/G beads at 4° C. for 2 hours, and the previously removed lysate was mixed with agarose beads conjugated with αFlag antibody at 4° C. for 4 hours. The precipitate was then extensively washed with lysis buffer. The protein bound to the beads was eluted and separated on a Nupage 4-12% Bis-Tris gradient gel (Invitrogen). Next, after silver staining (Invitrogen), a specific protein band was cut out and analyzed by ion-trap mass spectrometry at the mass spectrometry facility at the Korea Institute of Basic Science (Seoul), and tandem mass spectrometry and database search were performed. Amino acid sequences were determined through tandem mass spectrometry and database searches.

1-10. Quantitative Real-Time PCR

Total RNA was extracted from cells using RNeasy RNA extraction Mini-Kit (Qiagen), and cDNA was synthesized using Enzynomics kit (Enzynomics). Quantitative PCR was performed using a gene-specific primer set (Bioneer) and SYBR Green PCR Master Mix (Roche), and real-time PCR was performed using QuantStudio™3 (ABI) according to the manufacturer's protocol. The data were corrected for the expression level of β-actin, and the relative expression level of mRNA was calculated using the delta-delta Ct method. Sequence information of primers specific for each gene used in this PCR is shown in Table 1 below.

TABLE 1

| Gene | Diresction | Sequence (5'-3') | SEQ ID No. |
| --- | --- | --- | --- |
| mCD86 | Forward | gcacgtctaagcaaggtcac | 3 |
|  | Reverse | catatgccacacaccatccg | 4 |
| miNOS | Forward | ccccgctactactccatcag | 5 |
|  | Reverse | ccactgacacttcgcacaaa | 6 |
| mCD163 | Forward | tgtgaccatgctgaggatgt | 7 |
|  | Reverse | ctcgaccaatggcactgatg | 8 |
| mArg1 | Forward | ctgagctttgatgtcgacgg | 9 |
|  | Reverse | tcctctgctgtcttcccaag | 10 |
| mβ-Actin | Forward | aagtgtgacgttgacatc | 11 |
|  | Reverse | gatccacatctgctggaagg | 12 |

1-11. Confocal Fluorescence Microscopy

Immunofluorescence analysis was performed according to a known method. Specifically, cells were fixed on coverslips with 4% (w/v) paraformaldehyde diluted in PBS, and then permeabilized for 10 minutes using 0.25% (v/v) Triton X-100 at 25° C. Thereafter, the cells were treated with the primary antibody that specifically binds to TRAF6 or His, which was diluted 1/100, reacted at 25° C. for 1 hour, and washed. The cells were treated with an appropriate fluorescently-labeled secondary antibody, and then reacted at 25° C. for 1 hour. Then, the slides were observed with a laser scanning confocal microscope (model LSM 800; Zeiss).

1-12. Cell Fraction

Cytoplasm and mitochondria were isolated from cells using a mitochondrial fractionation kit (Active Motif, 40015) or according to a known method. Next, the intracellular protein fraction was dissolved in a buffer containing 2% SDS. 2× reducing sample buffer was added and the mixture was boiled, and SDS-PAGE was performed.

1-13. MTT Assay

Relative cell viability for the non-treated group was measured via MTT assay. More specifically, after culturing the cells for a set time period, a 5 mg/ml of MTT (3-(4,5-dimethylthiazol-2-yl)-2,5-diphenyltetrazolium bromide) solution was added instead of the medium, and the cells were further cultured for 4 hours. Thereafter, all the medium was removed, and formazan was dissolved by adding an equal volume of dimethyl sulfoxide (DMSO) solution for 15 minutes. Each well of the plate was measured at an absorbance of 540 nm using a UV/VIS spectrophotometer to measure the relative cell viability.

1-14. Flow Cytometry

Flow cytometry data were obtained via FACSCanto (BD Biosciences, San Diego, CA) and analyzed with FlowJo software (Tree Star, Ashland, OR). In order to check the expression of cell surface proteins, the cells were treated with the corresponding primary antibody and cultured at 4° C. for 20 to 30 minutes. Then the cells were fixed using Cytofix/Cytoperm Solution (BD Biosciences), some of which were cultured with antibodies so as to detect intracellular proteins. The primary antibodies used for this flow cytometry are as follows: NK1.1 (PK136, eBioscience), LY6G (1A8-Ly6g eBioscience), SR-A (PSL204, eBioscience), FcR (MAR-1, eBioscience), TLR2 (6C2, eBioscience), TLR4 (HTA125, eBioscience), NRP1 (3DS304M, eBioscience), and CXCR2 (eBio5E8-C7-F10 (5E8-C7-F10), eBioscience).

1-15. Statistical Analysis

All data were analyzed using Student's t-test with Bonferroni adjustment for multiple comparisons and expressed as mean±SD. Statistical analyzes were performed using the SPSS (version 12.0) statistical software program (SPSS, Chicago, IL, USA). Differences were considered statistically significant at p<0.05. For viability, the log-rank (Mantele-Cox) test for comparison using GraphPad Prism (version 5.0, La Jolla, CA, USA) was used to graph and analyze the data with the product restriction method of Kaplan and Meier.

Example 2. Confirmation of Interaction Between GRA9 and NLRP3

In order to confirm the function of *Toxoplasma gondii* (*T. gondii*) GRA9 in the host immune response of macrophages, the present inventors investigated whether GRA9 interacts with components related to inflammation. To this end, the GRA9 complex was co-immunoprecipitated with a vector or THP-1 cells containing Flag-GRA9.

As a result, it was confirmed that the immunoprecipitated and purified GRA9 complex included NLRP3 (118K) and metallothionein 2A (metallothionein 2A; MT2A, 6K) through mass spectrometry as shown in FIG. 1A. NLRP3 is known as a cytoplasmic receptor involved in the activation of immune responses in macrophages. Previous studies have reported that the GRA protein of *Toxoplasma gondii* interacts with host proteins related to immune cells and modulates the host immune system, but the interaction between GRA and NLRP3 has not been clearly identified.

Therefore, in order to investigate the correlation between NLRP3 and GRA9, the present inventors stimulated THP-1 cells through LPS treatment and activated them by treatment with ATP or nigericin, and then THP-1 cells that do not express GRA9 (THP-1-Vector) and THP-1 cells expressing GRA9 (THP-1-GRA9), respectively, were co-immunoprecipitated.

Figure 1B:
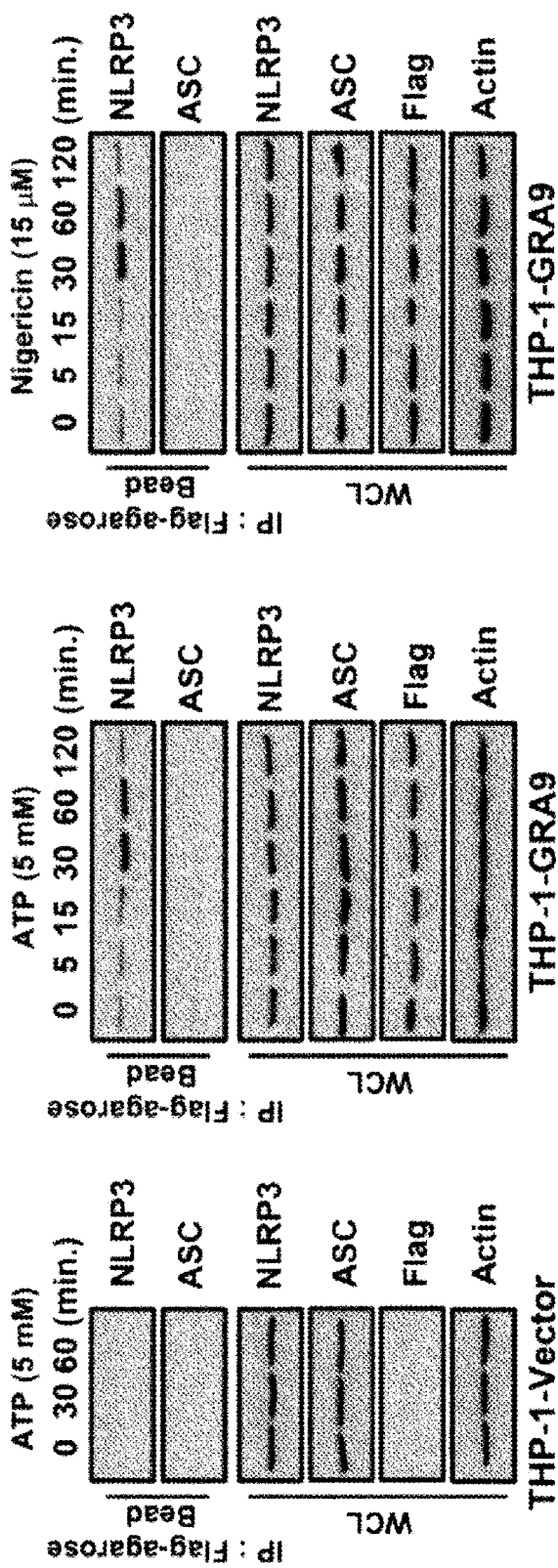

As a result, as shown in FIG. 1B, it was confirmed that when THP-1-GRA9 was stimulated with LPS and activated with ATP or nigericin, GRA9 strongly but transiently (30 to 60 minutes) interacted with the endogenous NLRP3 of the cell. These results showed that GRA9 interacted with NLRP3 in macrophages.

Example 3. Inhibition of NLRP3 Inflammasome Formation by Blocking Binding of ASC and Confirmation of Interaction Between GRA9 and NLRP3 in Mitochondria Mitochondria are organelles involved in the induction of recruitment of NLRP3 to construct the NLRP3 inflammasome in the mitochondria-related membrane (MAM) through the generation of mitochondrial reactive oxygen species. The present inventors confirmed that GRA9 is the binding partner of NLRP3, and thus they investigated the binding site in macrophages.

Figure 2A:
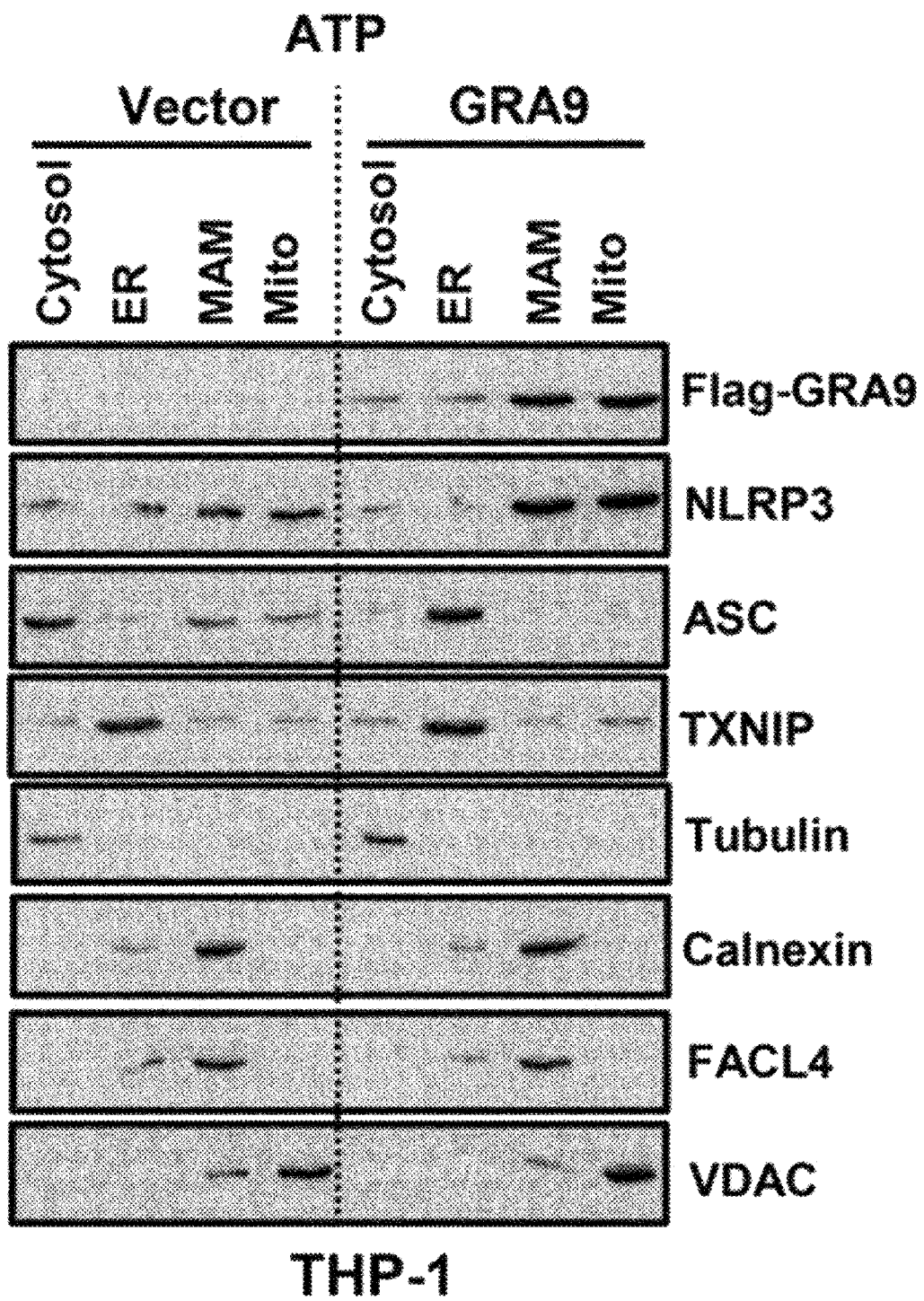
Figure 2B:
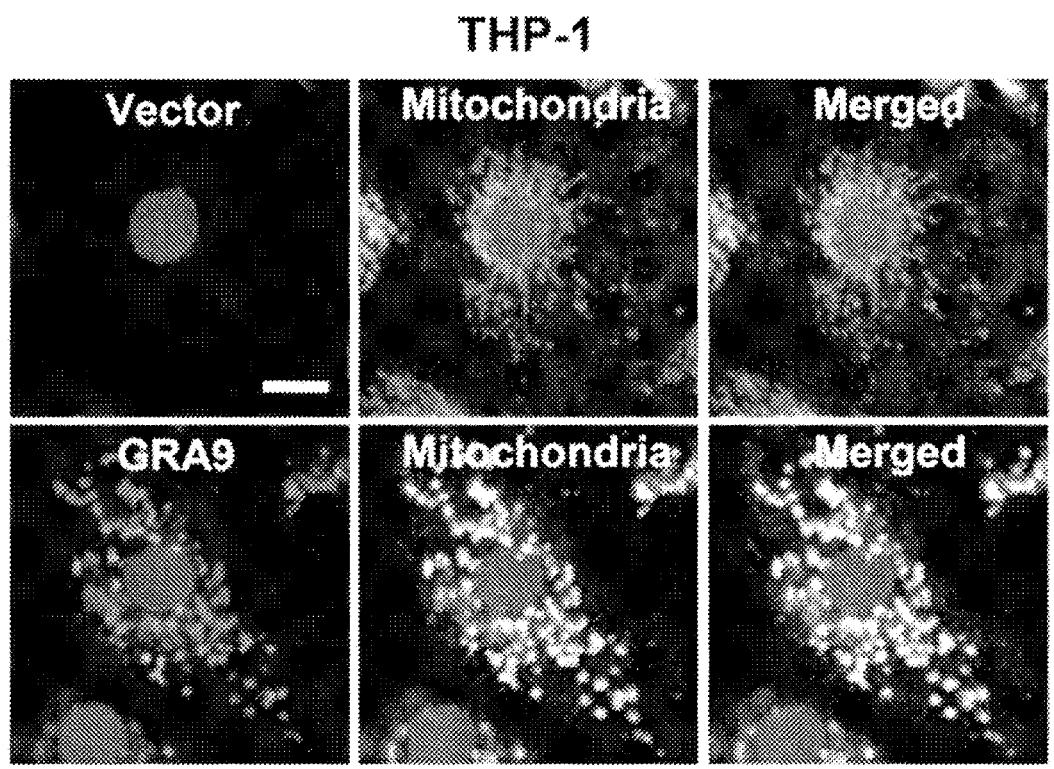

To this end, THP-1 cells were stimulated with LPS, activated by treatment with ATP, and then intracellular fractionation of organelles was performed. As a result, as shown in FIGS. 2A and 2B, it was confirmed cytosol, endoplasmic reticulum (ER), mitochondrial-related membrane (MAM) and mitochondrial (mito) fractions in GRA9-expressing THP-1 cells, respectively. The results indicated that GRA9 and NLRP3 were mainly located in MAM and mitochondria, respectively, through immunoblotting and fluorescence imaging.

Figure 2C:
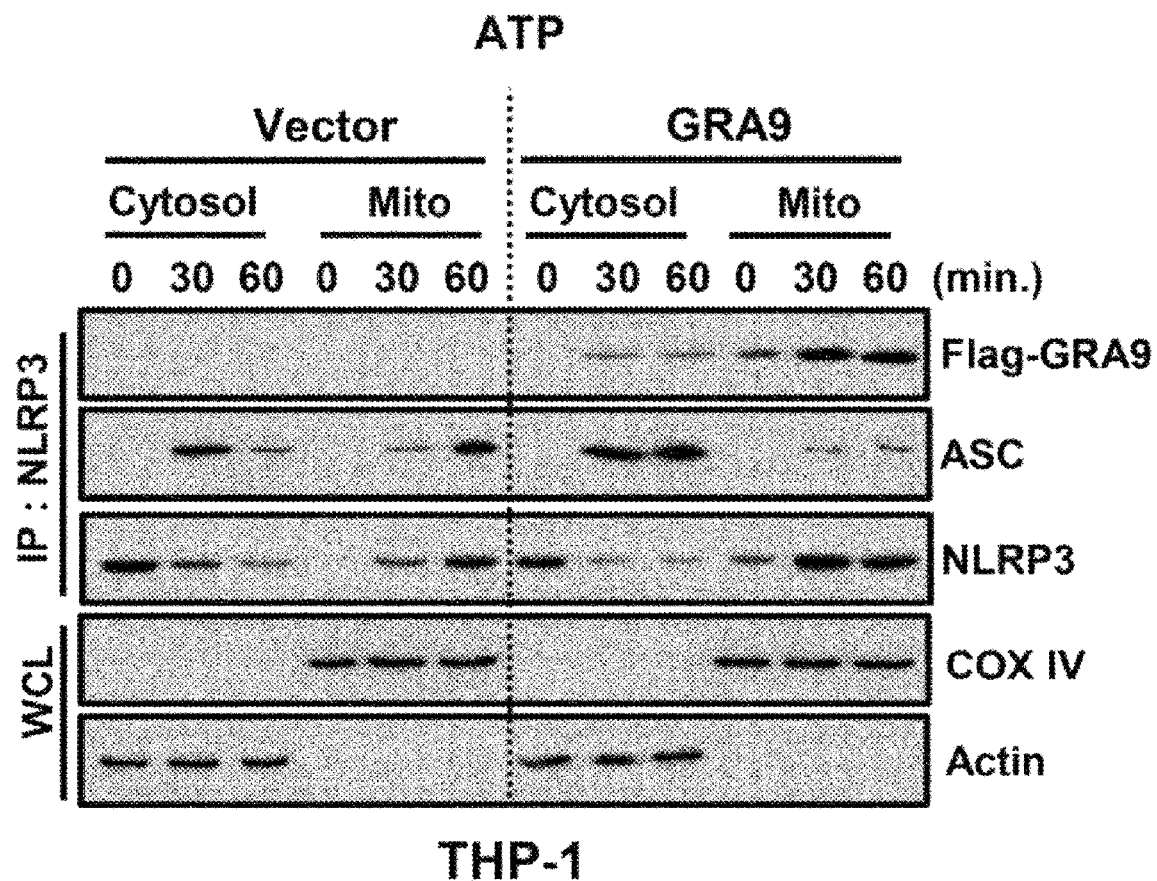
Figure 2D:
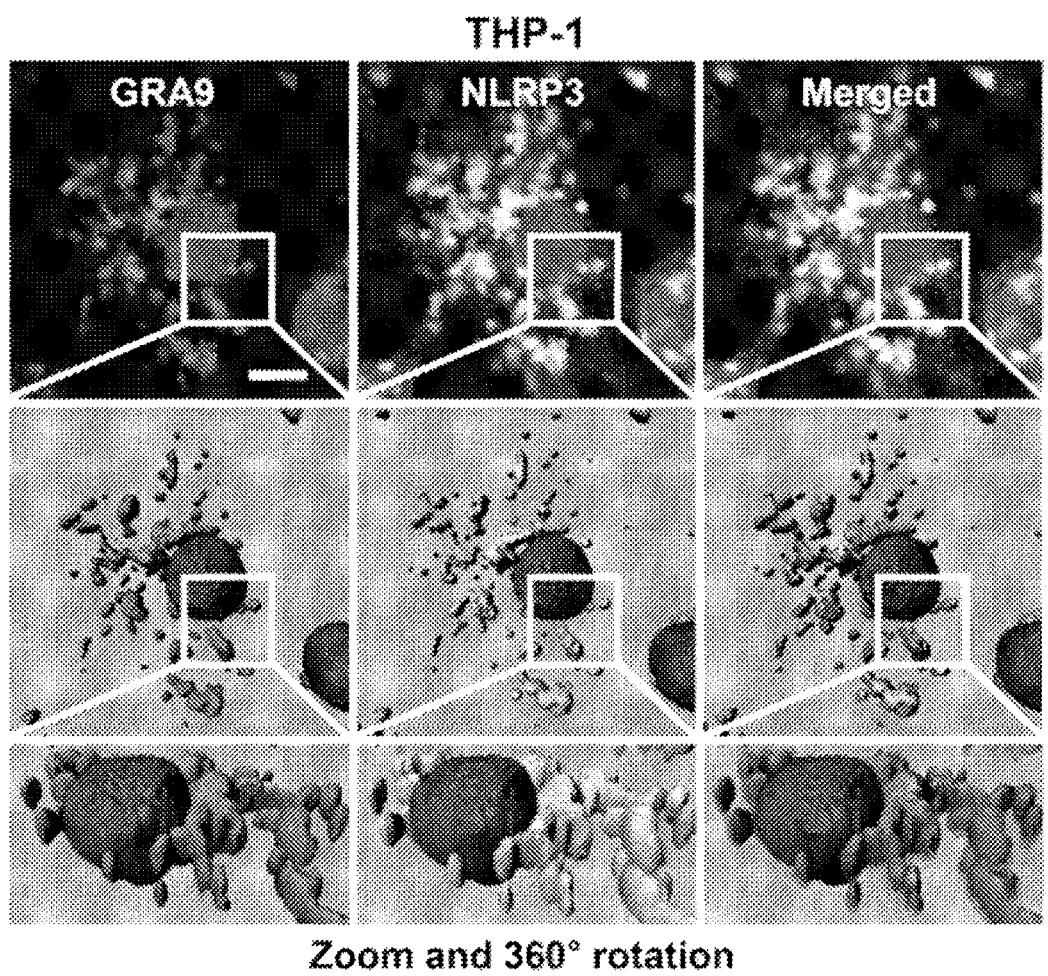

Furthermore, in order to confirm whether GRA9 interacts with NLRP3 in mitochondria, NLRP3 was immunoprecipitated from the cytoplasmic or mitochondrial fraction of the vector or GRA9-expressing THP-1 cells. As a result, as shown in FIG. 2C, GRA9 was found to interact in the mitochondria, not in the cytoplasm, as well as inhibit the binding of ASCs interacting with NLRP3 so as to generate NLRP3 inflammasome. Further, consistent with the result of FIG. 2C, it was also observed that NLRP3 and GRA9 co-localized at the same location through the fluorescence imaging result of THP-1 cells of FIG. 2D.

Figure 2E:
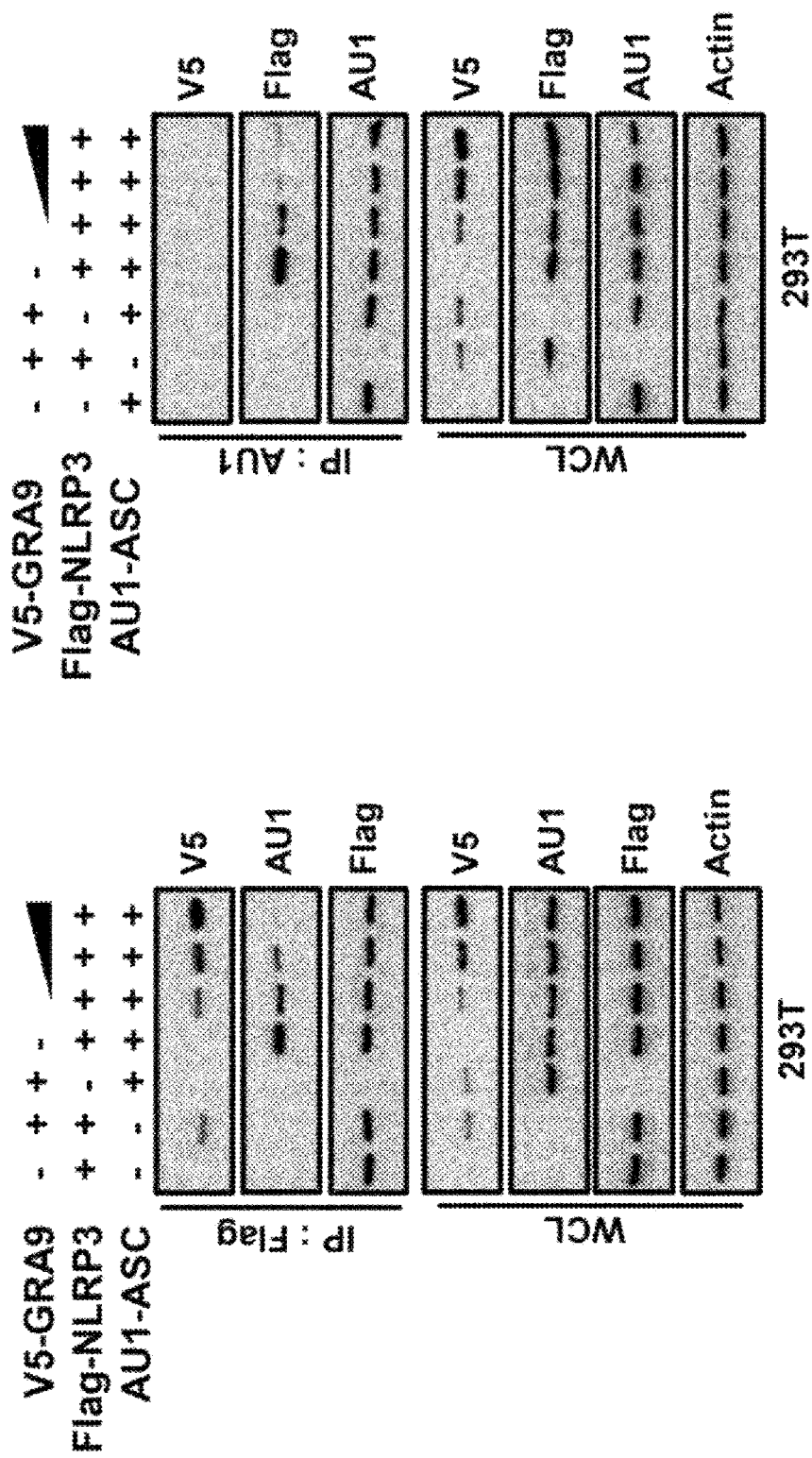

In order to verify the results in FIG. 2C, the present inventors transfected 293T cells with V5-GRA9, Flag-NLRP3 and AU1-ASC plasmids, and then immunoprecipitated with Flag or AU1, respectively. As a result, as can be seen in FIG. 2E, it was confirmed that GRA9 interacted with NLRP3 and ASC binding was inhibited in proportion to the expression level of GRA9.

These results indicate that GRA9 acts as a binding partner of NLRP3 while competitively inhibiting the binding of ASC to NLRP3 in mitochondria.

Example 4. Confirmation of Inhibition of GRA9's C-Terminal Mediated NLRP3 Inflammasome Activation The present inventors investigated a more specific interaction domain between GRA9 and NLRP3 in macrophages from the results confirmed in Example 3, and for this purpose, a method of immunoprecipitating wild-type or mutant GRA9 and NLRP3 was used.

Figure 3A:
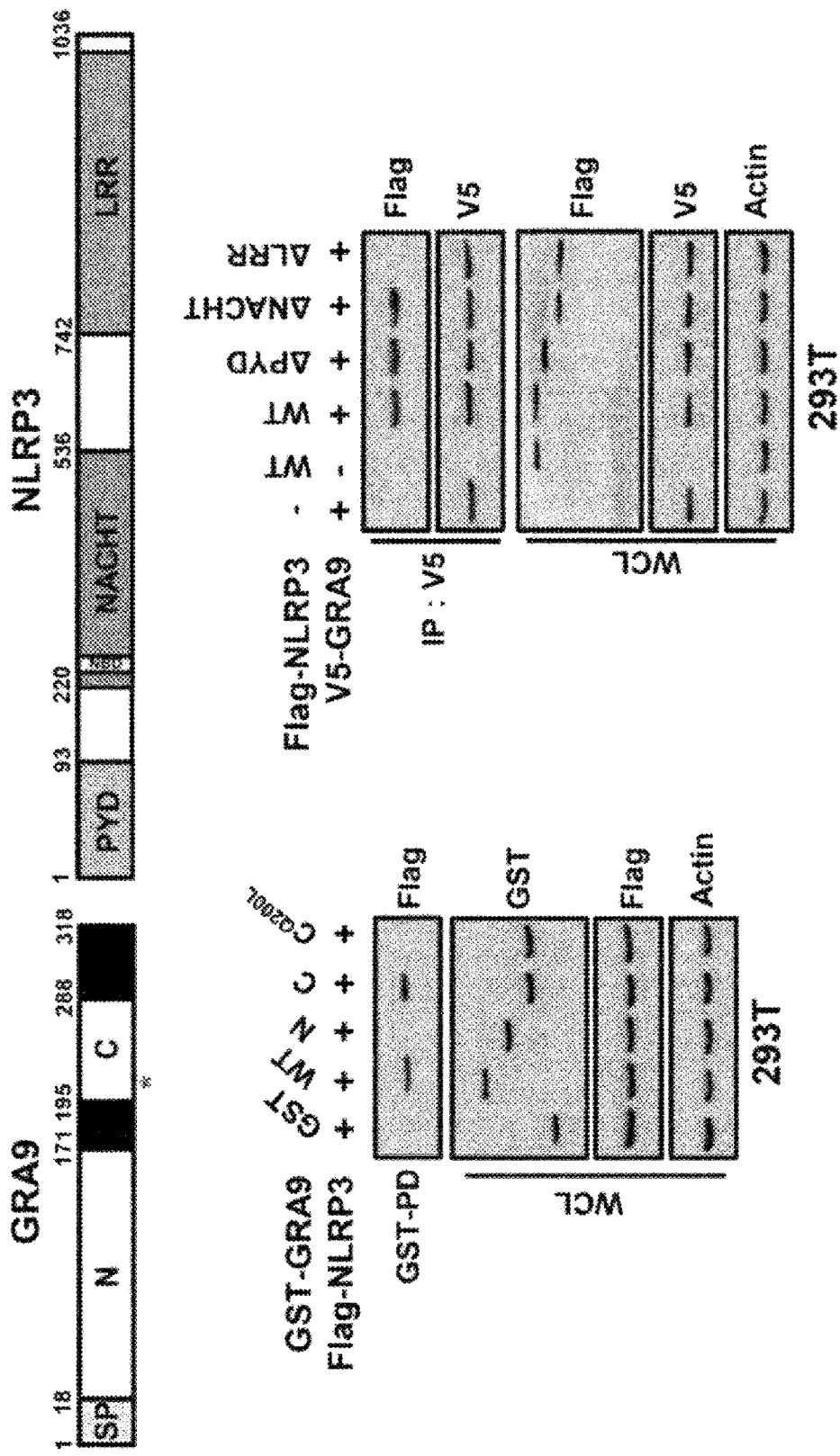

As shown in FIG. 3A, the GRA9 protein includes a signal sequence (SP), an N-terminal domain (amino acids (aa) 18-171) and a C-terminal domain (aa 195-288). In 293T cells, domain mapping was performed using truncated mutants of GST-GRA9 or Flag-NLRP3 together with wild-type Flag-NLRP3 or V5-GRA9 and various fusion sites. As can be seen in FIG. 3A, the C-terminal domain (C) of GRA9 had minimal binding affinity with NLRP3, and the LRR domain of NLRP3 (aa 742-1036) bound to GRA9 as strong as wild-type (WT) NLRP3. Additionally, it was confirmed that GST-GRA9 containing the Q200L mutation at the C-terminus did not bind to NLRP3. These results suggest that glutamine (Q) at position 200 at the C-terminus of GRA9 is essential for the interaction between GRA9 and NLRP3.

The formation of NLRP3 inflammasomes with ASC and pro-caspase 1 is induced with activation of immune responses in host cells. Caspase 1 is a truncated form of pro-caspase 1, which is known to be important for the cleavage of IL-1β and IL-18 secreted from macrophages. Accordingly, the present inventors performed immunoblotting to investigate the specific role of GRA9 in macrophages and measured the expression level of cytokines related to inflammation.

Figure 3B:
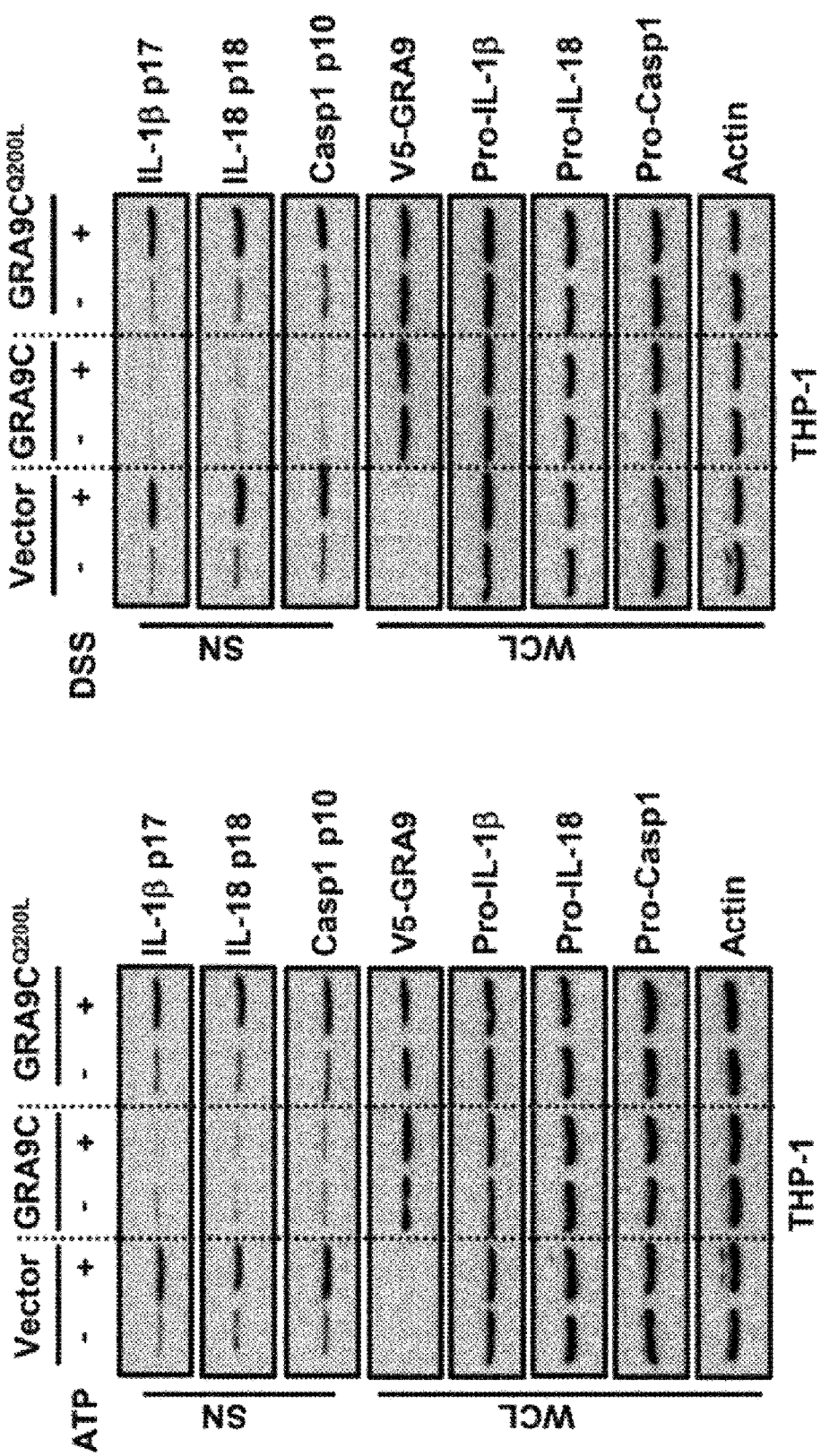

First, THP-1 cells expressing the vector, the C-terminus of GRA9 (GRA9C), and the C-terminus of GRA9 (GRA9C$^{Q200L}$) containing the Q200L mutation, respectively, were stimulated with LPS and activated by treatment with ATP or DSS, respectively. After cell culture, immunoblotting was performed using cell culture supernatant (SN) and whole cell lysate (WCL) to compare and analyze the cleavage and secretion patterns of caspase 1, IL-1β and IL-18 proteins. As shown in FIG. 3B, the results confirmed that GRA9C-expressing THP-1 cells reduced the secretion of Casp 1 p10, IL-1β p17 and IL-18 p18 protein, which were truncated forms of caspase 1, IL-1β and IL-18, respectively, compared to vector-expressing cells and GRA9C$^{Q200L}$-expressing cells.

Figure 3C:
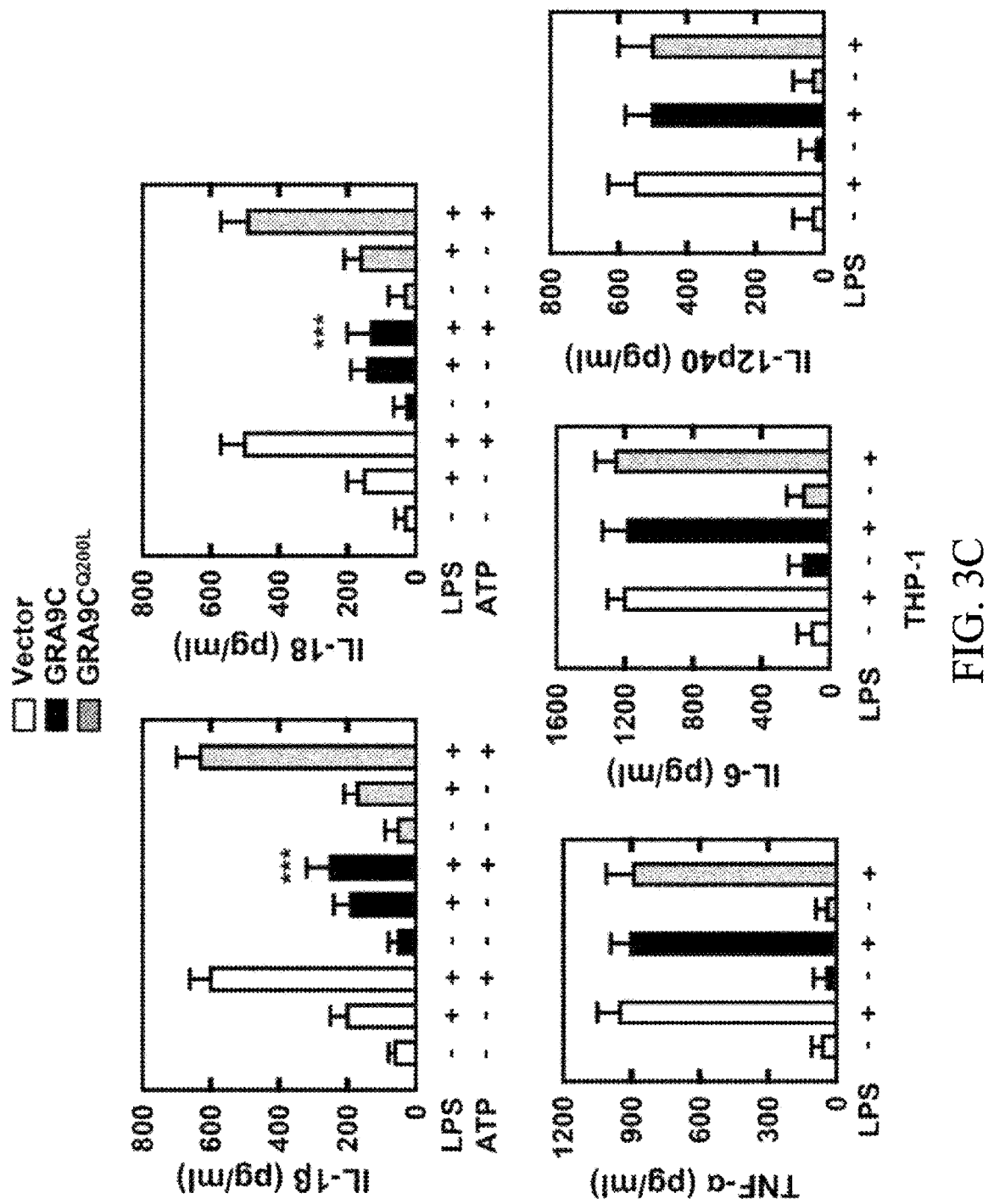

Next, as a result of measuring the expression levels of cytokines IL-1β, IL-18, TNF-α, IL-6 and IL-12, which are cytokines related to inflammation in each THP-1 cell identical to the above, interestingly, as shown in FIG. 3C, the amounts of TNF-α, IL-6 and IL-12 did not show a significant difference in GRA9C-expressing THP-1 cells compared to vector and GRA9C$^{Q200L}$-expressing cells. These results suggest that the interaction between GRA9C and NLRP3 is related only to the activation step of the NLRP3 inflammasome.

Combining the above results, it can be seen that GRAS, particularly the C-terminus containing the Q200 residue, is essential for interaction with NLRP3 and inhibits the formation of NLRP3 inflammasome to reduce the inflammatory response induced by NLRP3.

Example 5. Confirmation of NLRP3-Mediated Inflammation Reduction Through Interaction of rGRA9C with NLRP3

Figure 4A:
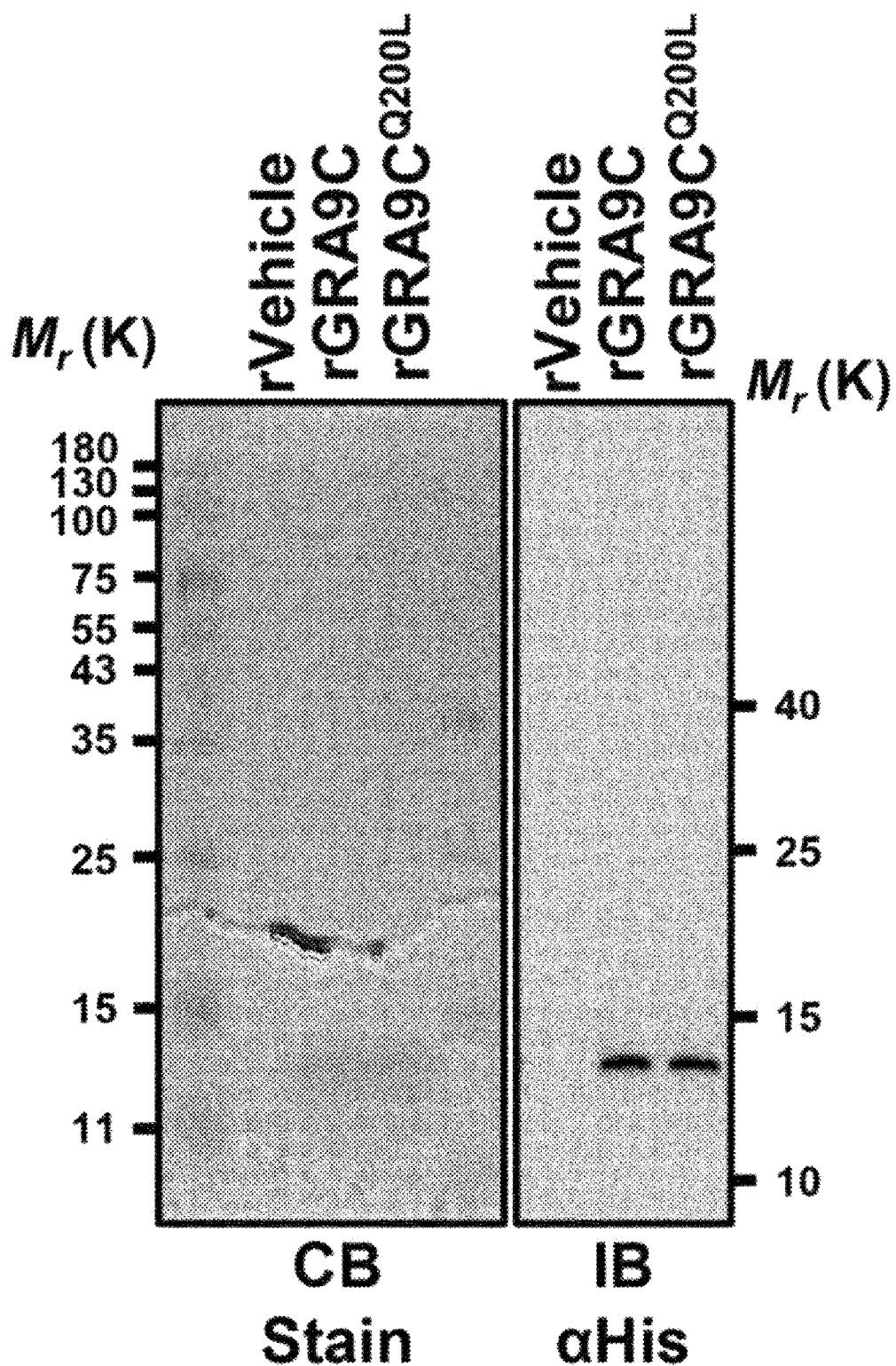

The present inventors confirmed the function of GRA9C identified in the above examples under physiological conditions. For this, rGRA9C or rGRA9C$^{Q200L}$ protein bound to His tag purified from bacteria was prepared. As shown in FIG. 4A, SDS-polyacrylamide gel electrophoresis and immunoblotting were performed to confirm the prepared protein. Next, primary bone marrow-derived macrophages (BMDMs) isolated from mice to be used in the following experiments were treated with rGRA9C- and rGRA9C$^{Q200L}$.

Figure 4B:
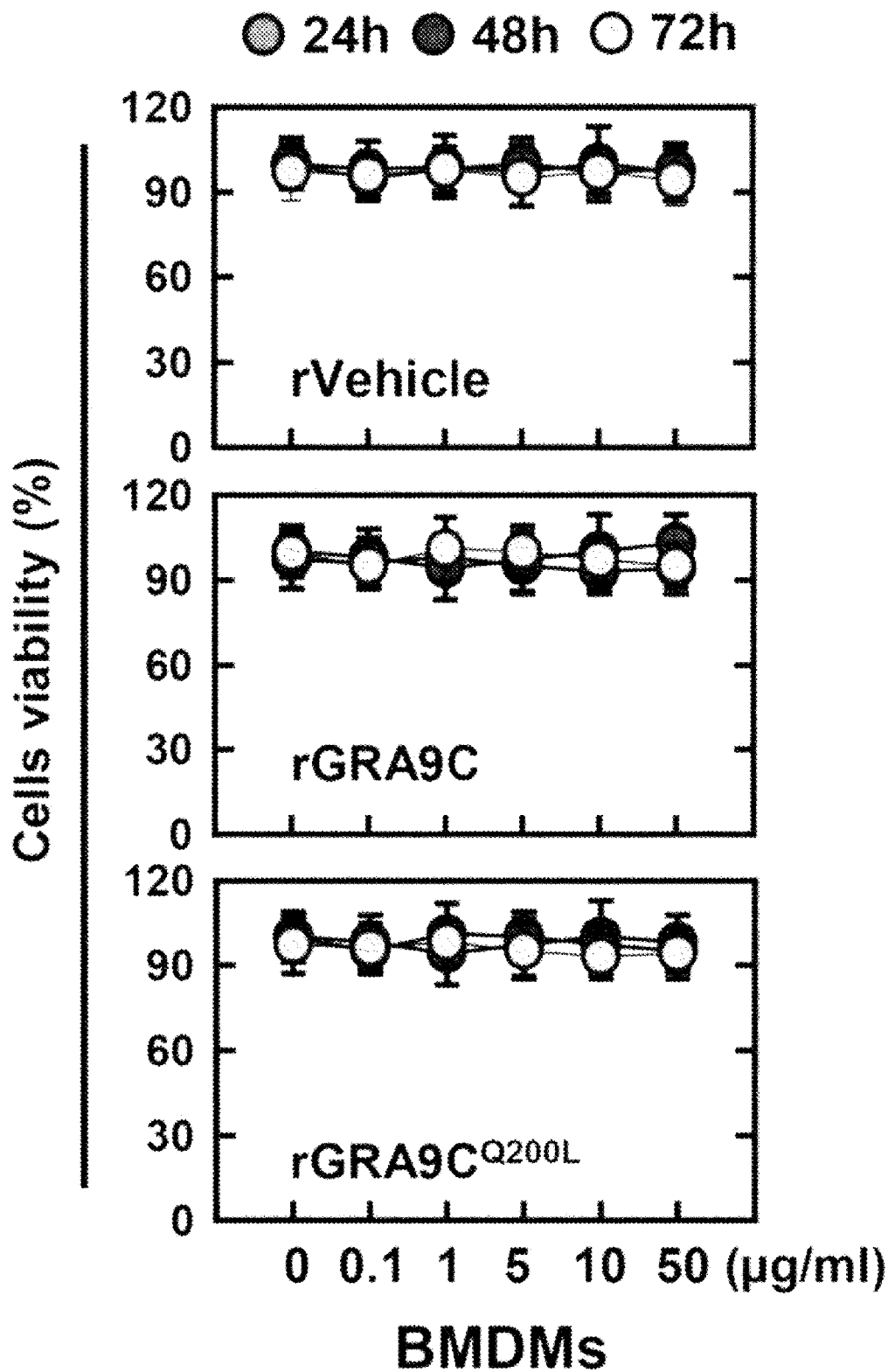

Cell viability was measured to verify whether cytotoxicity was induced. As shown in FIG. 4B, the results indicate that there was no significant difference compared with the vector control group (rVehicle).

Figure 4C:
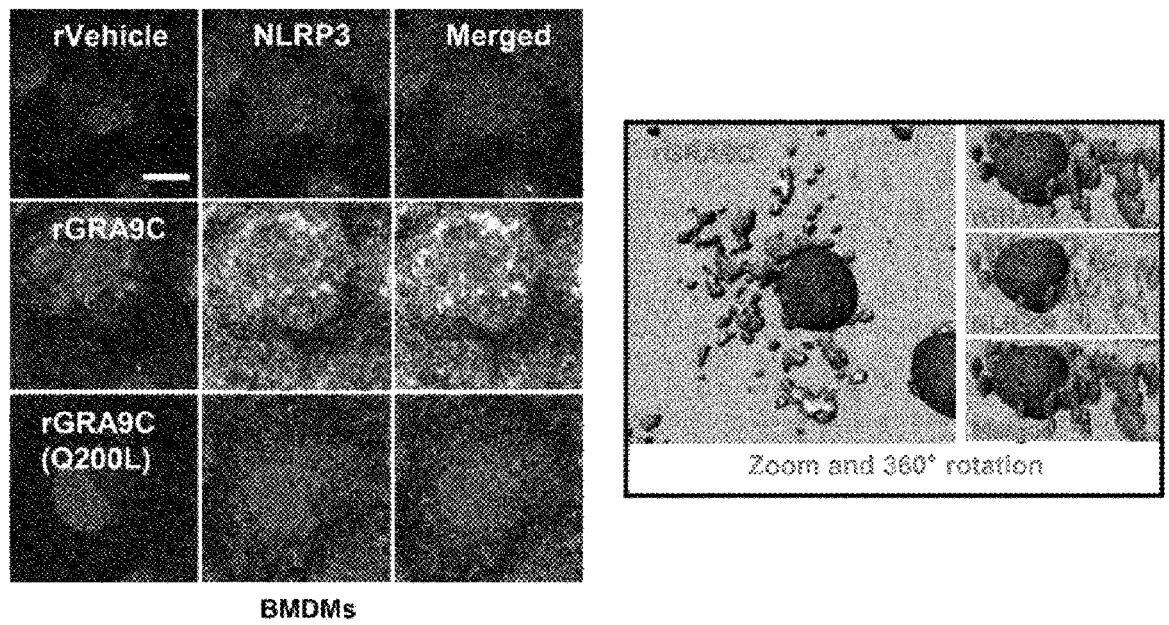

Therefore, the present inventors first treated the BMDMs with rGRA9C and observed the location of the rGRA9C protein through confocal microscopy images. As shown in FIG. 4C, the results indicate that rGRA9C was present in the same position as NLRP3, consistent with the result of FIG. 2D, whereas rGRA9C$^{Q200L}$ was not. Furthermore, in order to investigate whether rGRA9C regulates NLRP3-induced inflammation in macrophages, BMDMs were treated with LPS and ATP to induce priming and activation of the NLRP3 inflammasome and treated with rVector, rGRA9C or rGRA9C$^{Q200L}$. Then immunoprecipitation was carried out.

Figure 4D:
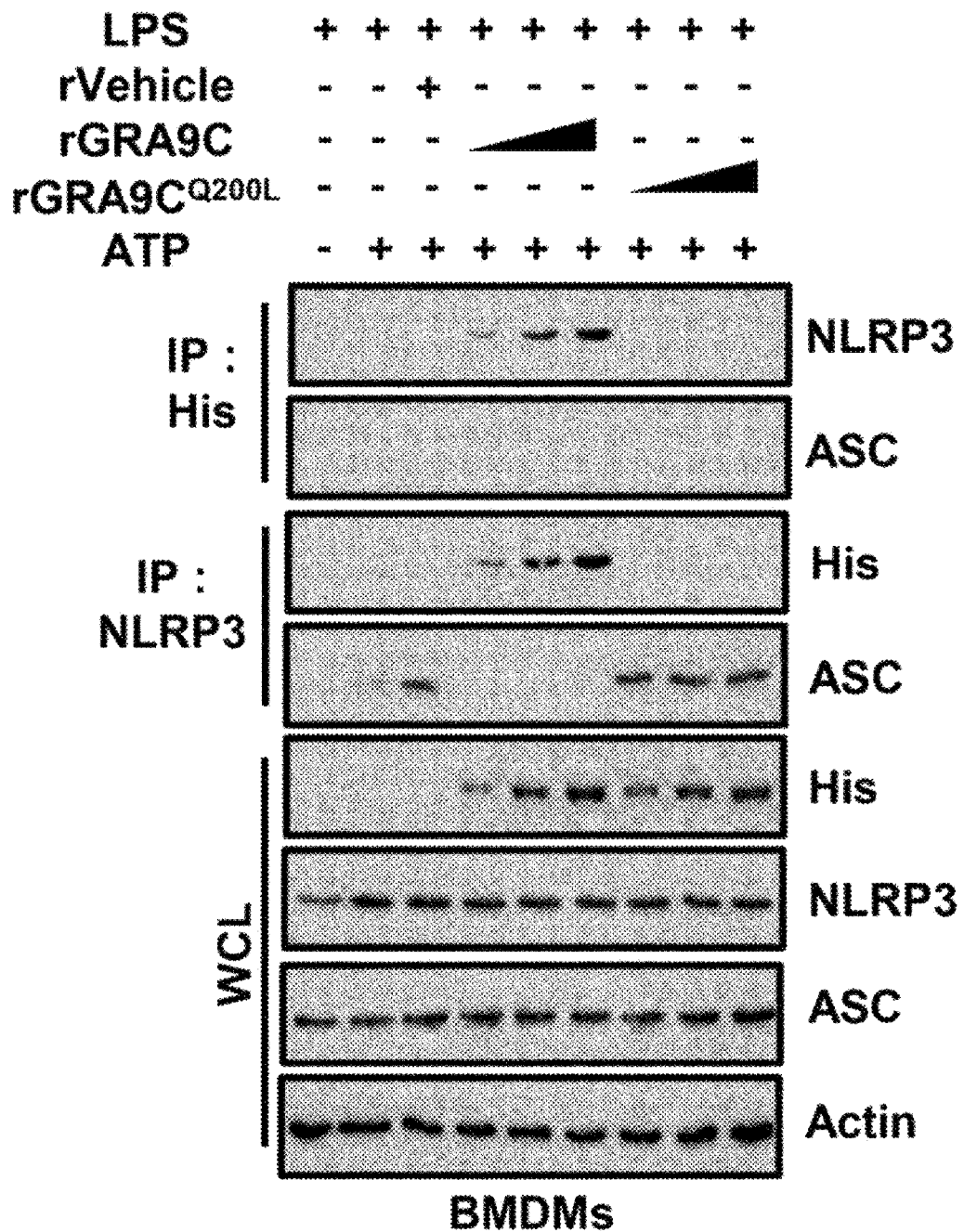
Figure 4E:
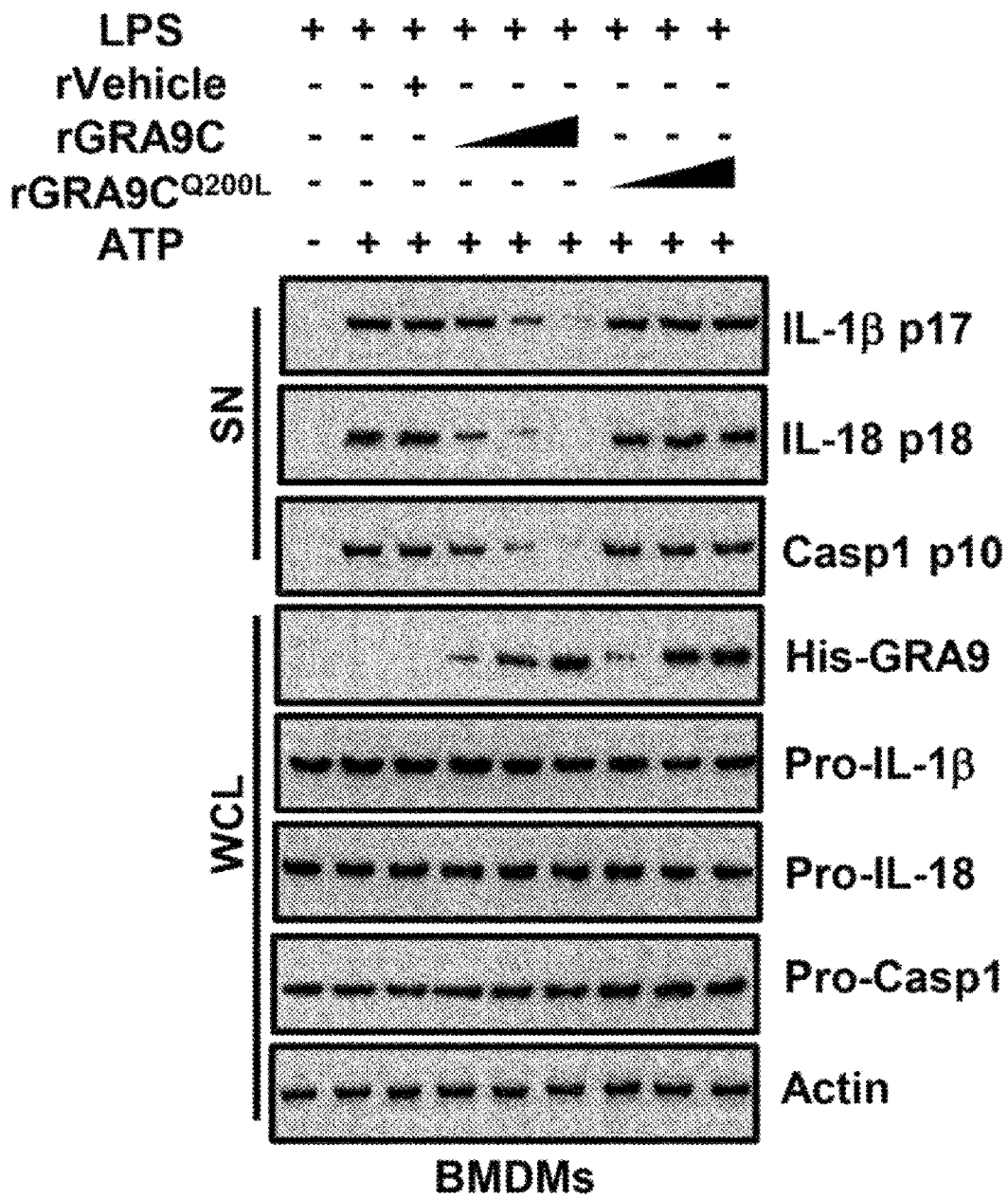
Figure 4F:
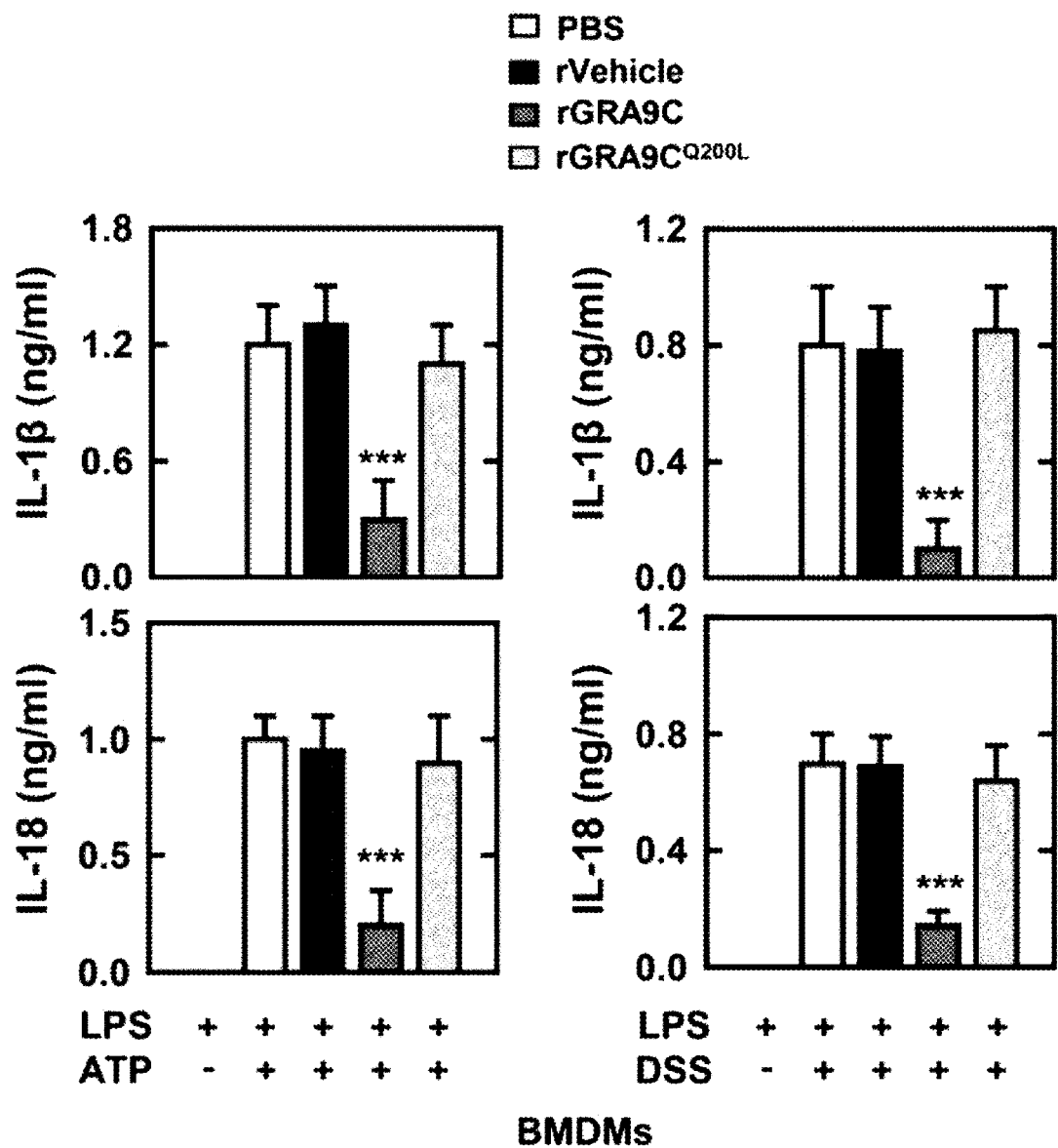

As shown in FIG. 4D, the results indicate that rGRA9C interacted with NLRP3 by inhibiting the binding of NLRP3 and ASC in proportion to the treatment concentration, but rGRA9C$^{Q200L}$ did not bind to NLRP3, as consistent with the results of FIGS. 3A to 3C. Further, as shown in FIG. 4E, it was confirmed that the secretion and cleavage of IL-1β, IL-18 and caspase 1 were inhibited only when BMDMs were treated with rGRA9C. Further, as shown in FIG. 4F, it was confirmed that the levels of IL-1β and IL-18 were significantly decreased by rGRA9C treatment in BMDMs stimulated with LPS, and ATP or DSS, but not when treated with rGRA9C$^{Q200L}$, similar to the above results.

Combining the above results, it can be seen that rGRA9C reduces NLRP3-mediated inflammation through interaction with NLRP3 in macrophages.

Figure 5A:
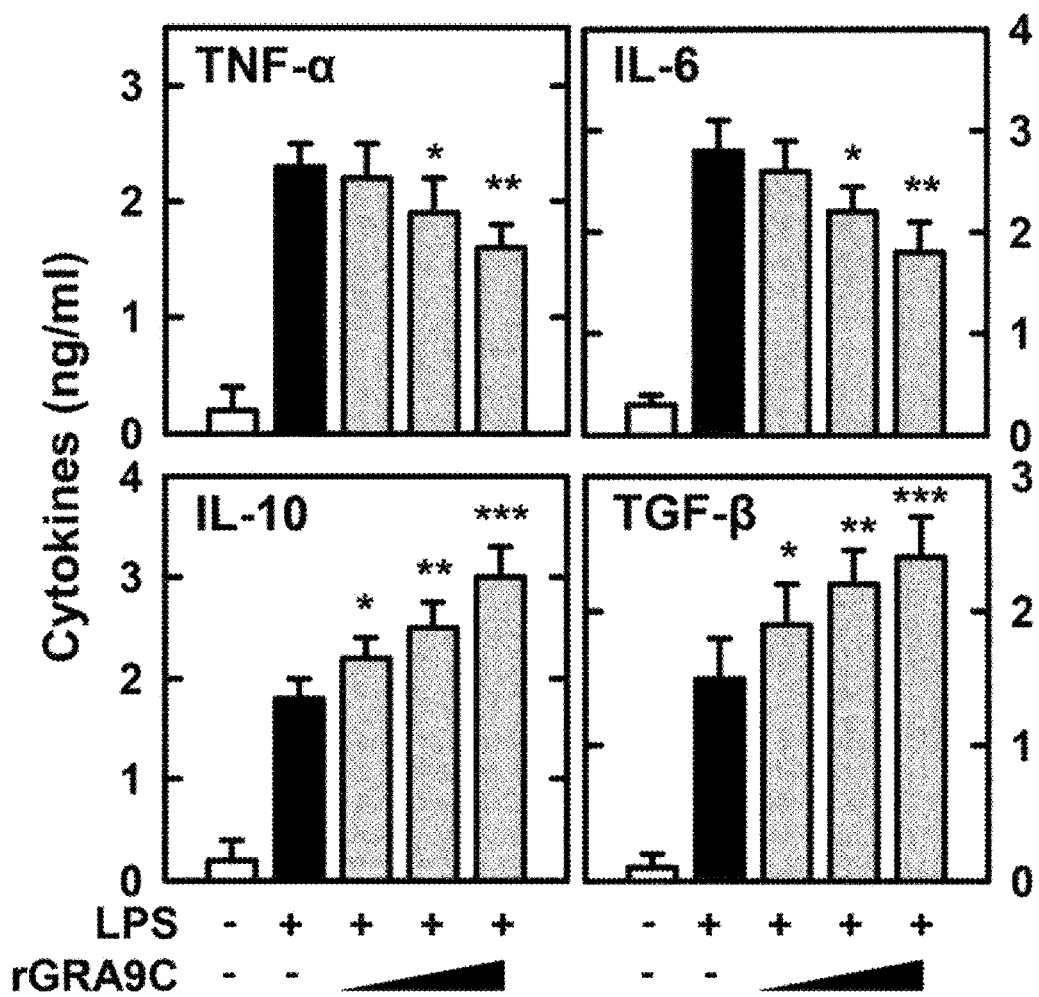

Example 6. Confirmation of Improvement of Anti-Inflammatory and Antibacterial Effect Through Polarization from M1 to M2 by rGRA9C Macrophages are essential for the innate immune response and play important roles including phagocytosis, inflammatory activation and wound healing. In order to find the effect of GRA9C related to macrophage function, the present inventors treated LPS-treated BMDMs with rVehicle, rGRA9C or rGRA9C$^{Q200L}$ at various concentrations and then measured the levels of inflammatory and anti-inflammatory cytokines through ELISA. As shown in FIG. 5A, unlike in the result of FIG. 3C, the results indicate that rGRA9C partially significantly reduced the level of inflammatory cytokines (TNF-α and IL-6) in proportion to the treatment concentration and increased levels of anti-inflammatory cytokines (IL-10 and TGF-β).

Figure 5B:
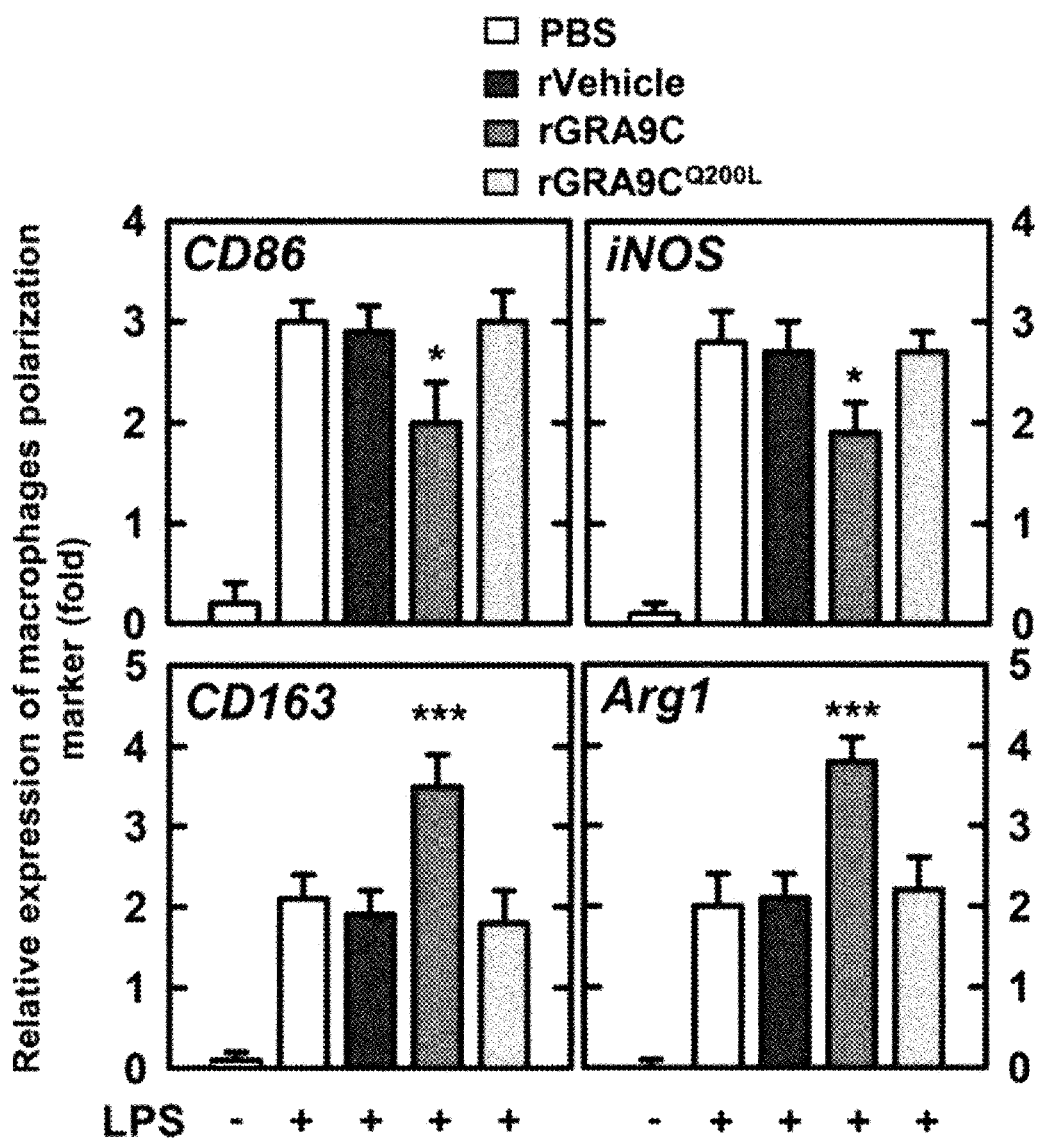
Figure 5C:
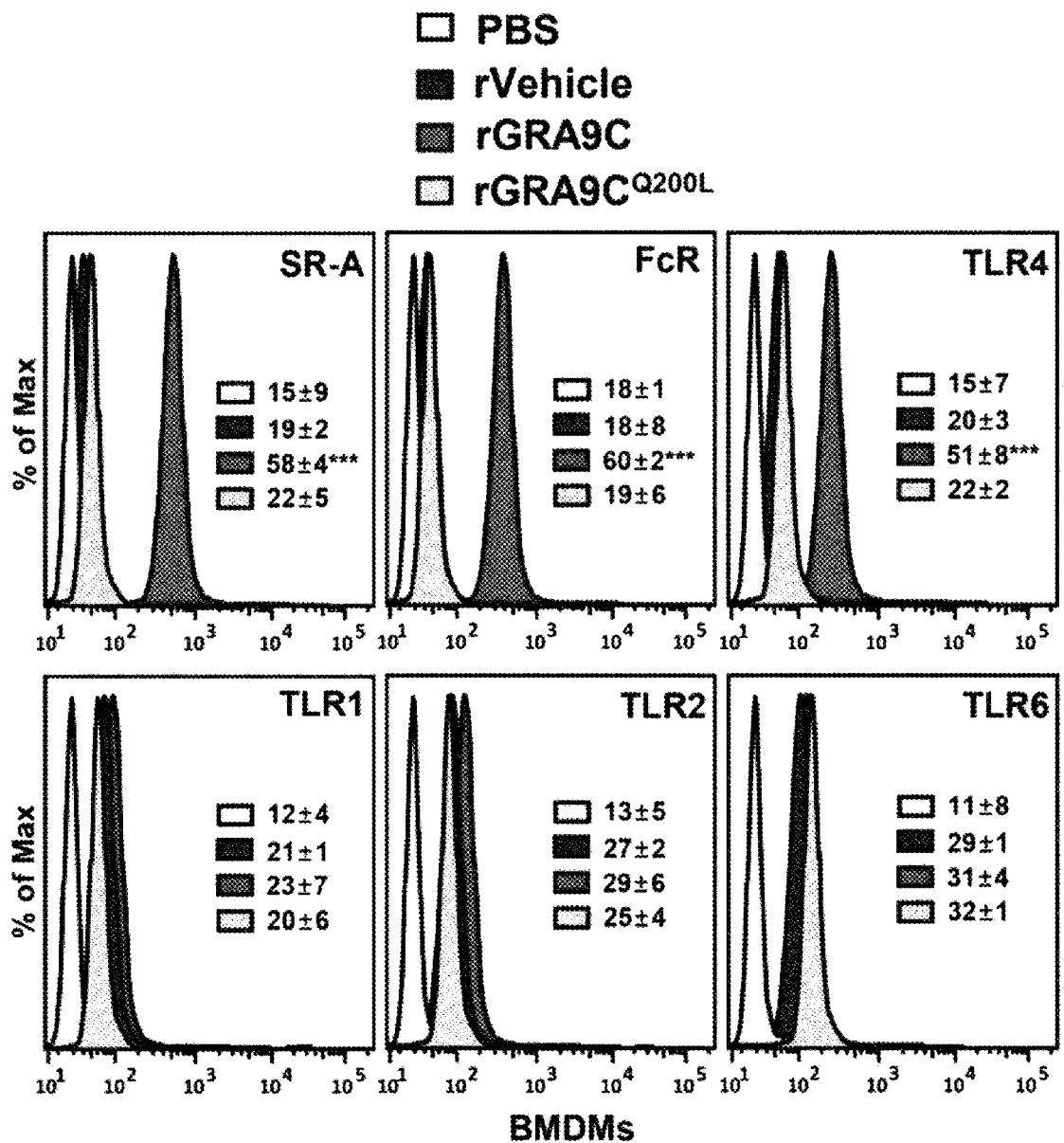

Based on the above results, the present inventors investigated whether rGRA9C is related to macrophage polarization based on the fact that the role of macrophages is differentiated depending on M1 or M2 polarization. To this end, BMDMs were treated with PBS, Vector, GRA9C, and GRA9C$^{Q200L}$, respectively, and then the relative expression levels of M1 markers (CD86 and iNOS) and M2 markers (CD163 and Arg1) were measured and analyzed. As shown in FIG. 5B, the results indicate that when rGRA9C was treated, a decrease in M1 markers (CD86 and iNOS) and an increase in M2 markers (CD163 and Arg1) were observed, but no change was observed in the remaining treatment groups. In addition, as shown in FIG. 5C, the expression of Scavenger A (SR-A) and Fc receptor (FcR) related to phagocytosis was significantly increased only in rGRA9C-treated cells. Interestingly, TLR4 expression was increased but TLR2 and TLR6 were unchanged. The results demonstrate that rGRA9C is involved in regulating the role of macrophages by converting M1 to M2 macrophages.

Figure 5D:
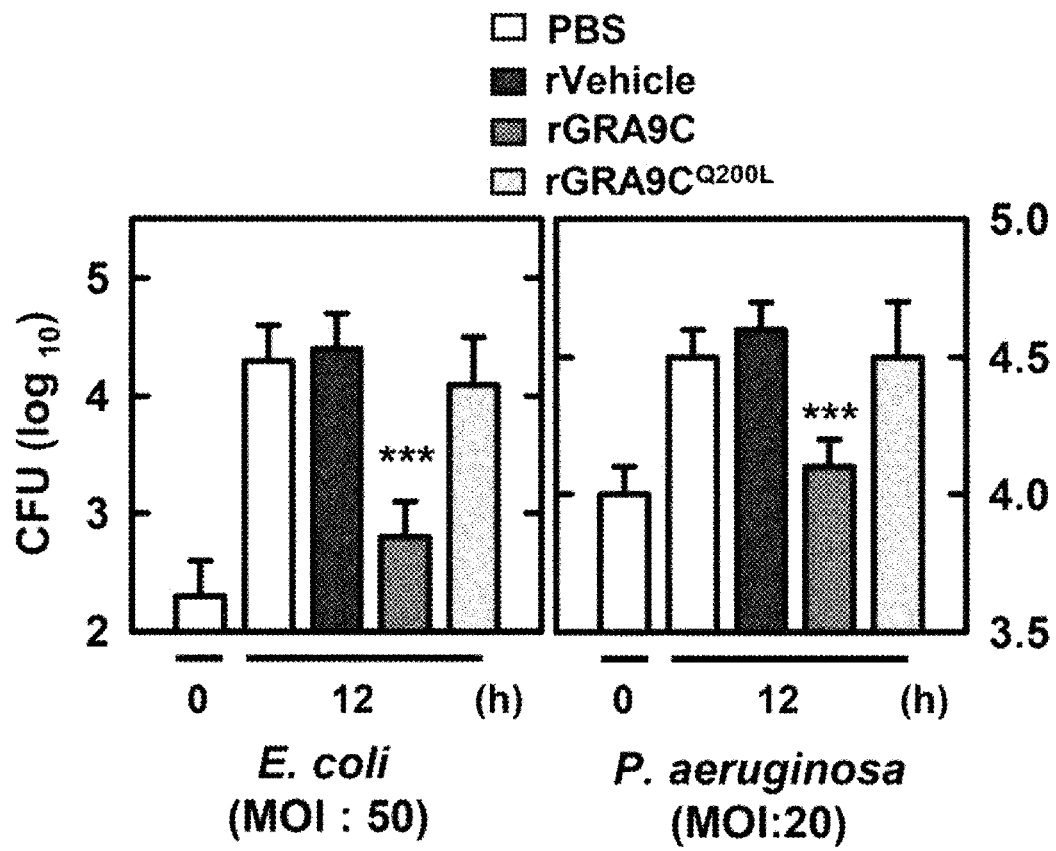
Figure 5E:
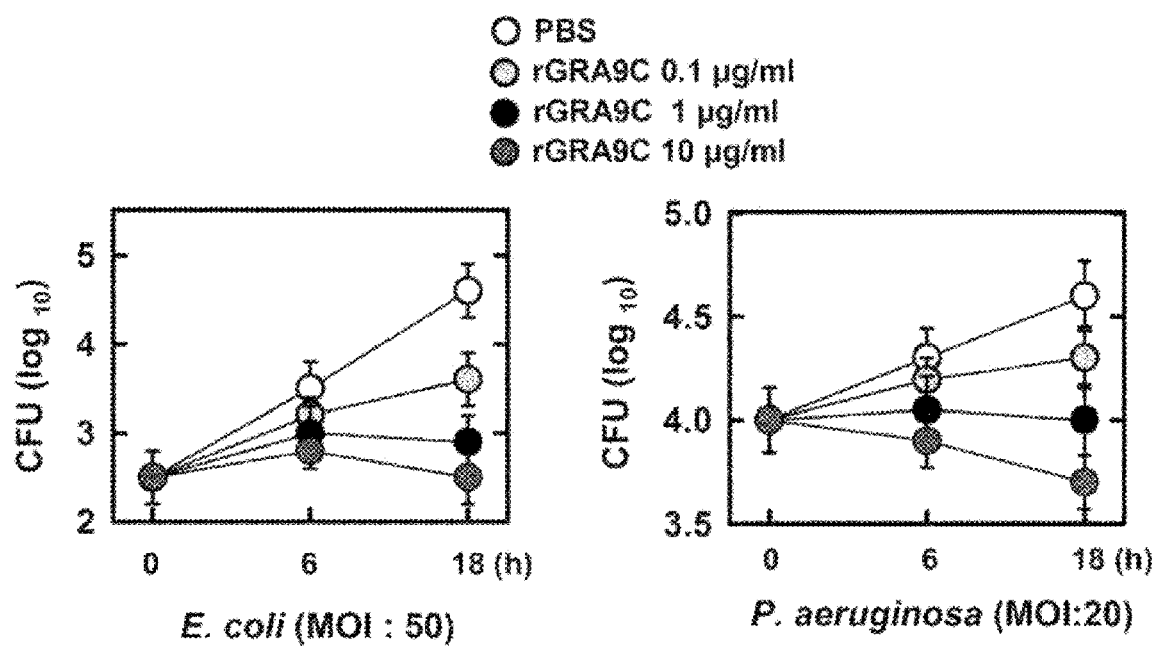

In addition, the present inventors investigated whether GRA9C mediates antibacterial effects in macrophages upon bacterial infection. As shown in FIGS. 5D and 5E, the results indicate that *E. coli* and *P. aeruginosa* in rGRA9C-treated BMDMs were significantly removed in proportion to the rGRA9C treatment concentration (0.1, 1, 10 µg/ml). In contrast, in the case of rGRA9C$^{Q200L}$, there was no effect of removing bacteria.

The above results show that rGRA9C not only regulates the activation of NLRP3 inflammasome through interaction with NLRP3 but also regulates the function of macrophages. In conclusion, it was found that rGRA9C increases M2 polarization and phagocytosis, thereby increasing the anti-inflammatory and antibacterial effects of macrophages.

Example 7. Confirmation of Protective Effect of rGRA9C in CLP and Bacterial-Infected Sepsis Mice The present inventors investigated whether rGRA9C could protect mice from septic shock due to multiple microbial peritonitis, which induces systemic inflammatory response syndrome and is usually fatal in humans, using either cecal ligation and puncture (CLP) or bacterial infection models of multiple microbial infections.

7-1. Validation of Effect of rGRA9C in CLP Sepsis Mice

Figure 6A:
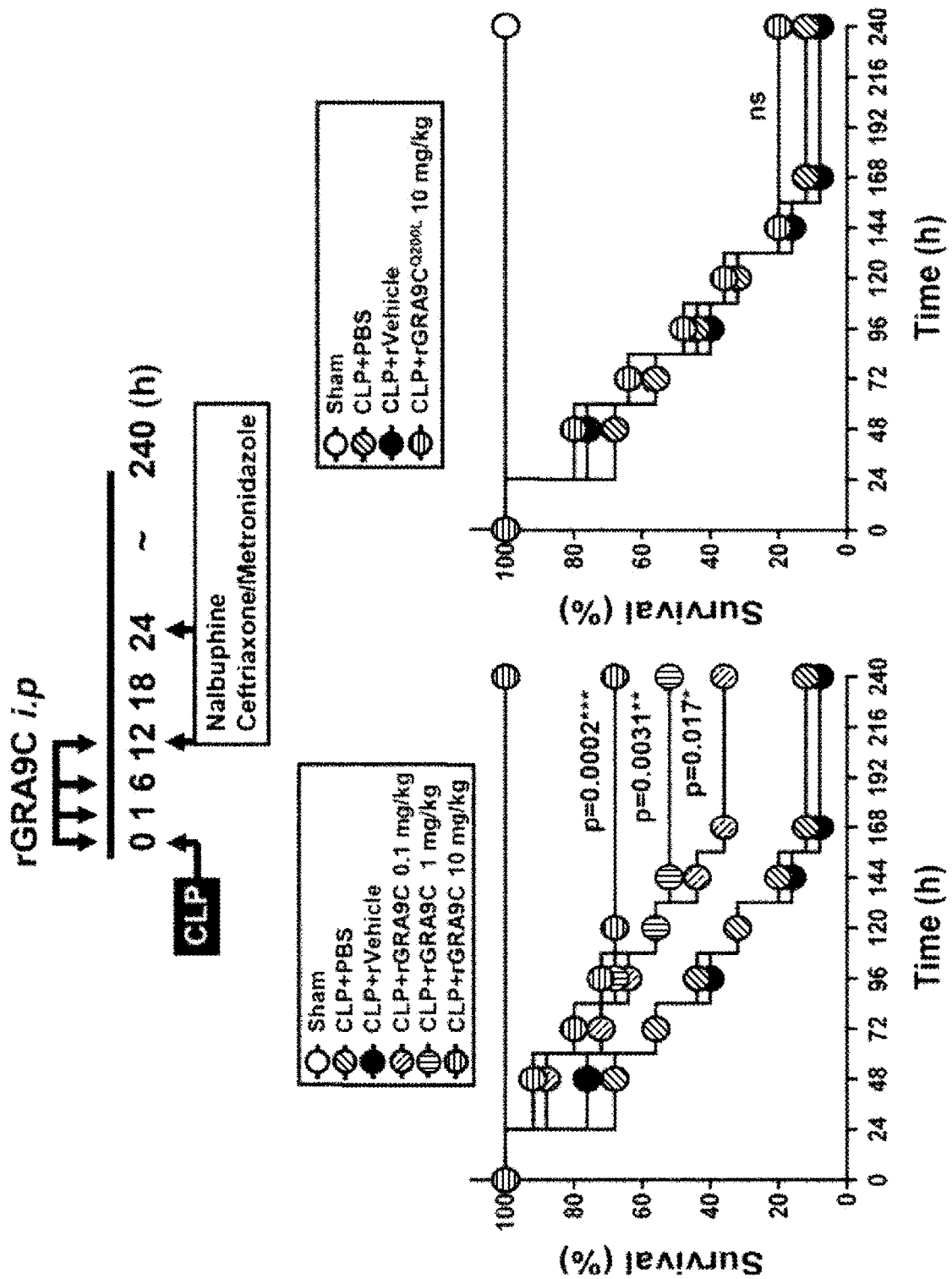

First, the protective effect of rGRA9C and mutants on death due to CLP septic shock in mice was tested. Specifically, a sepsis model through CLP was prepared, and PBS, Vehicle, rGRA9C or rGRA9C$^{Q200L}$ was intraperitoneally administered to the mouse model as shown in FIG. 6A, and rGRA9C was administered at various concentrations.

Figure 6B:
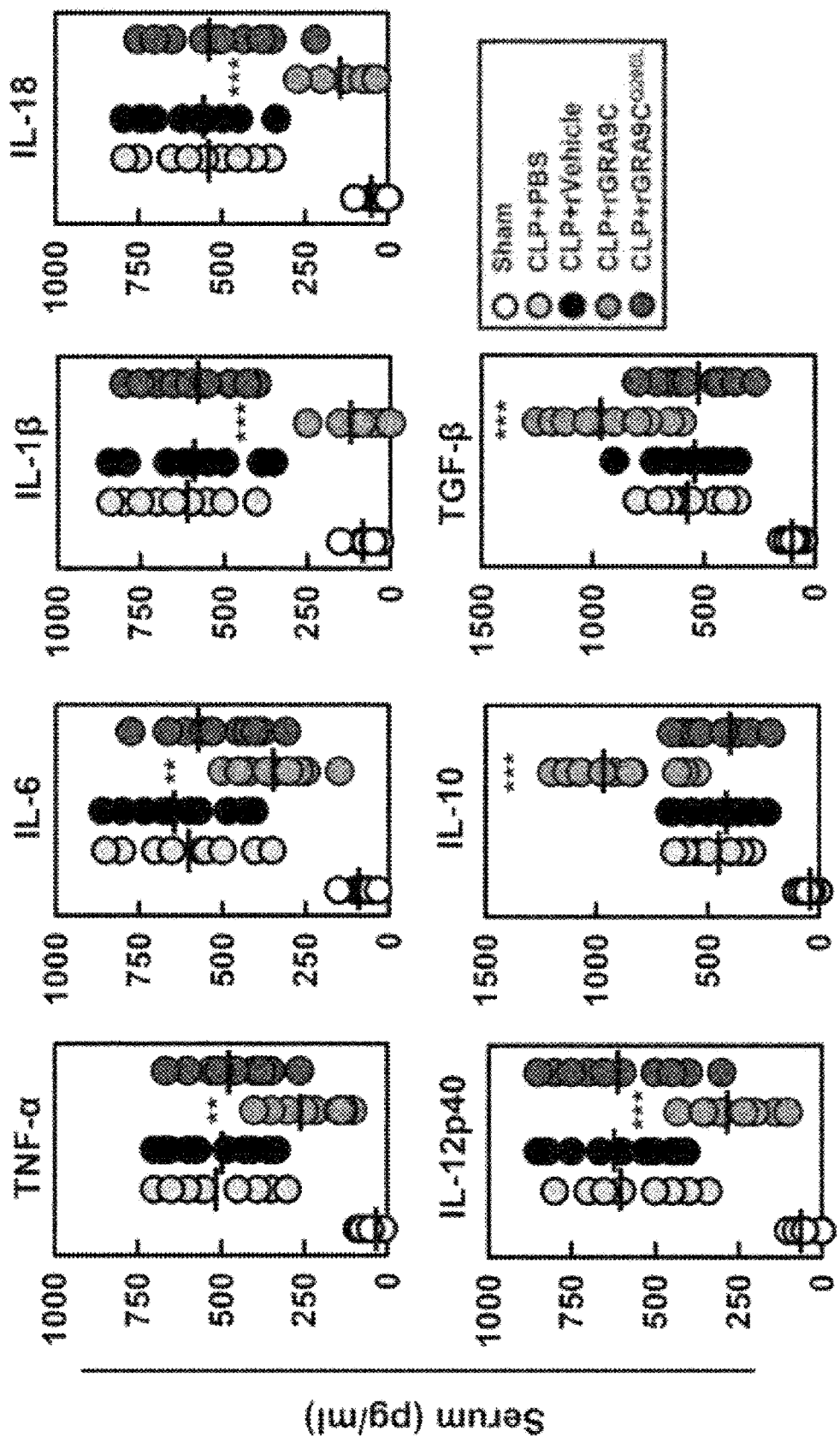

As a result, in the case of rGRA9C-administered mice (CLP+GRA9C), compared to the control group, the survival rate was proportionally increased at all administration concentrations (0.1, 1 and 10 mg/kg), thereby showing that it protects the mice from CLP-induced septic shock. However, in the case of GRA9C$^{Q200L}$-administered mice (CLP+GRA9C$^{Q200L}$, 10 mg/kg), this protective effect did not appear. Further, as a result of measuring the cytokine levels in the serum in each mouse group, as shown in FIG. 6B, the levels of inflammatory cytokines including TNF-α, IL-6, IL-1β, IL-18 and IL-12p40 in rGRA9C-administered mice (CLP+GRA9C) were decreased, but the levels of anti-inflammatory cytokines including IL-10 and TGF-β were increased.

Figure 6C:
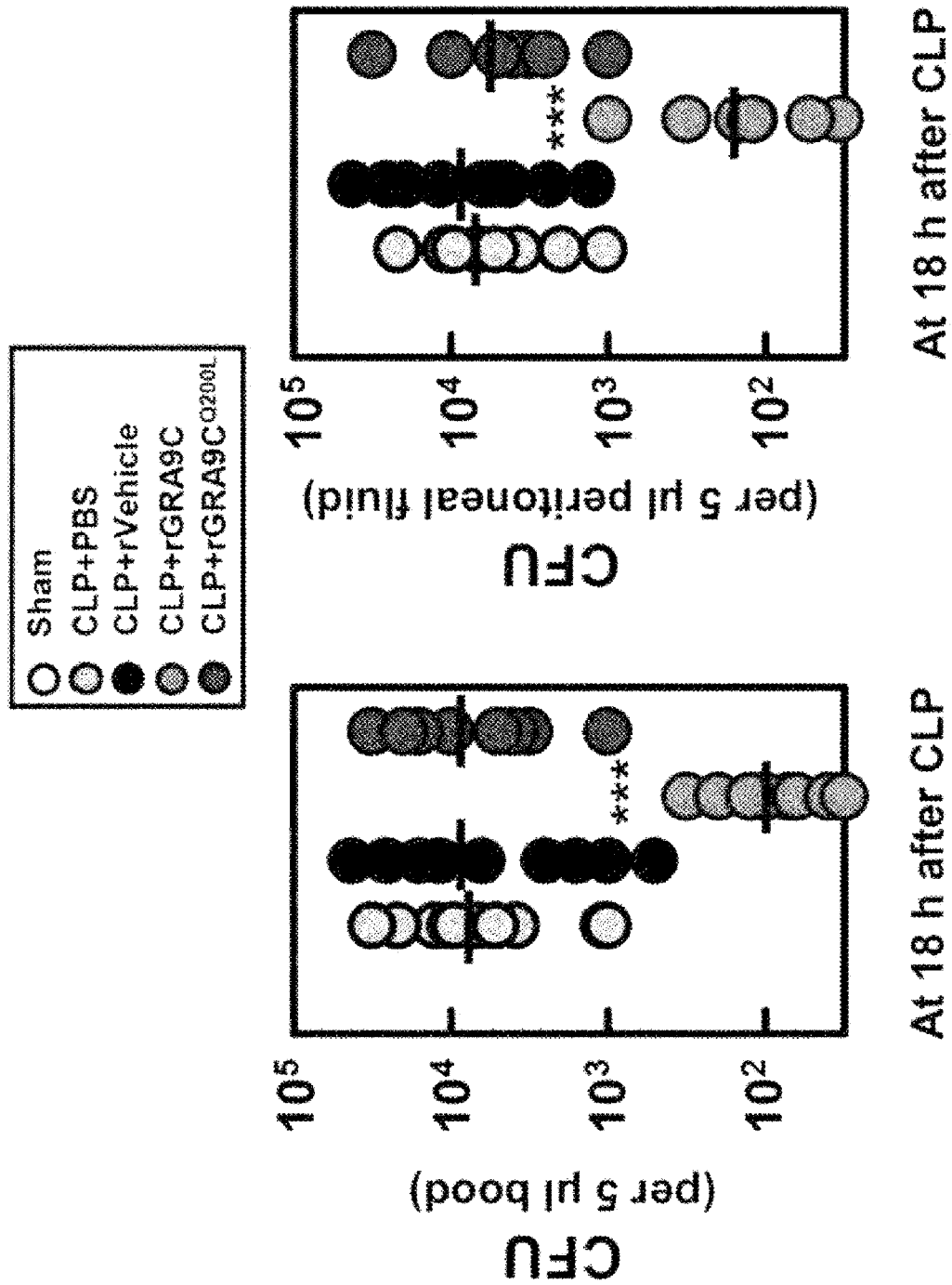
Figure 6D:
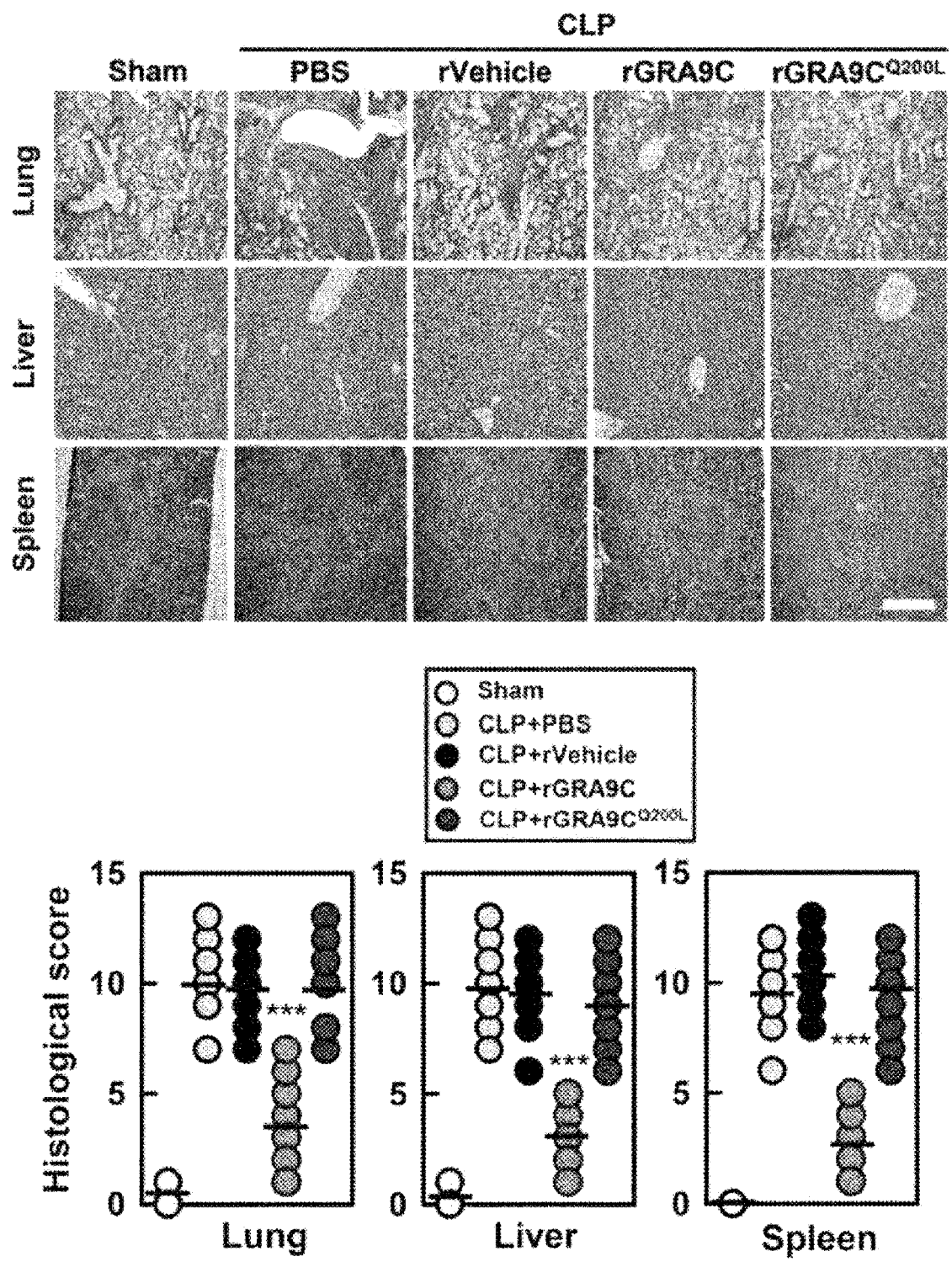
Figure 6E:
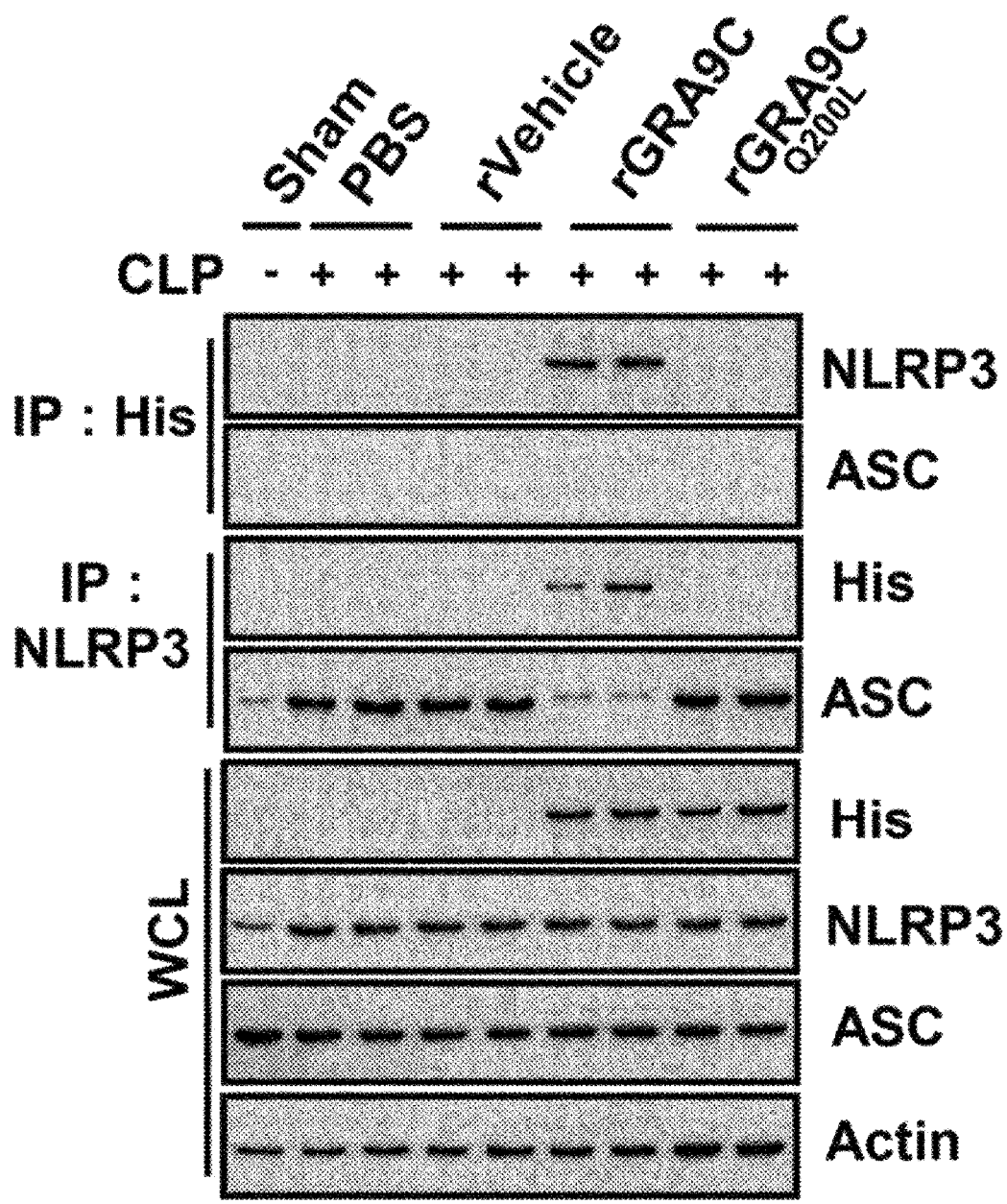

In addition to the above results, as shown in FIG. 6C, the results of examining the bacterial removal effect indicate that the bactericidal effect in the peritoneal fluid and blood was significantly increased as a result of administering rGRA9C to CLP mice (CLP+GRA9C). These results were also supported through reduced infiltration and reduced tissue damage of immune cells obtained by hematoxylin and eosin staining of the lung, liver, and spleen tissues of FIG. 6D. In addition, immunoprecipitation was performed using splenocytes of rGRA9C-treated mice. As shown in FIG. 6E, it was confirmed at the molecular level that rGRA9C interacted with NLRP3 while inhibiting the binding of NLRP3 to ASC, similar to the results in THP-1 or BMDMs.

Figure 6F:
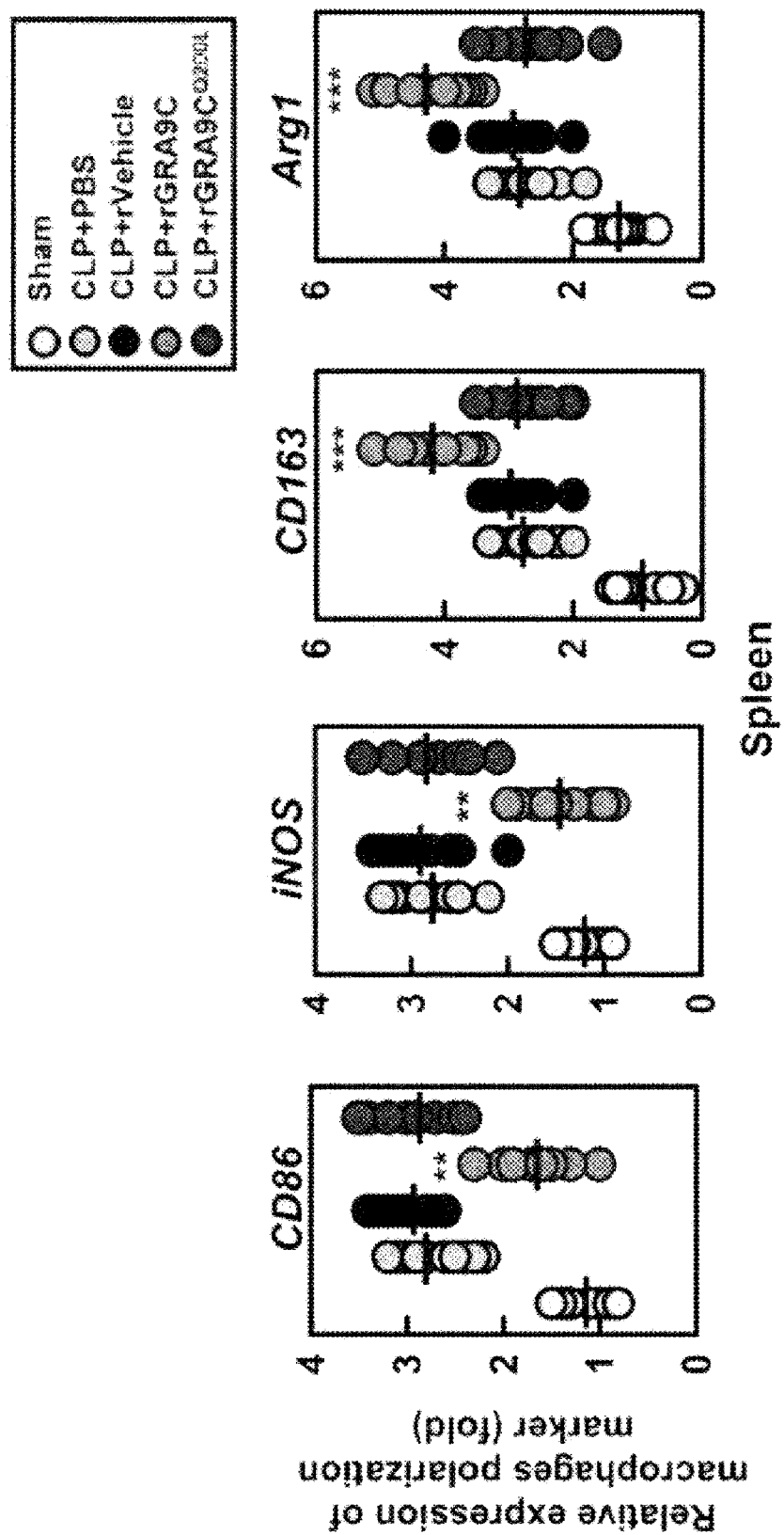

Additionally, the present inventors evaluated whether GRA9C was specifically associated with macrophages only or with other immune cells. As a result, interestingly, the number of macrophages was significantly increased in CLP sepsis mice administered with rGRA9C, but there was no significant difference in other immune cells. In addition, as shown in FIG. 6F, the expression levels of M1 markers (CD86 and iNOS) and M2 markers (CD163 and Arg1) in the mouse spleen were confirmed to indicate that the polarization from M1 to M2 macrophages was increased in the case of CLP-induced mice administered with GRA9C (CLP+GRA9C).

7-2. Validation of Effect of rGRA9C in Bacterial Sepsis Mice

Figure 7A:
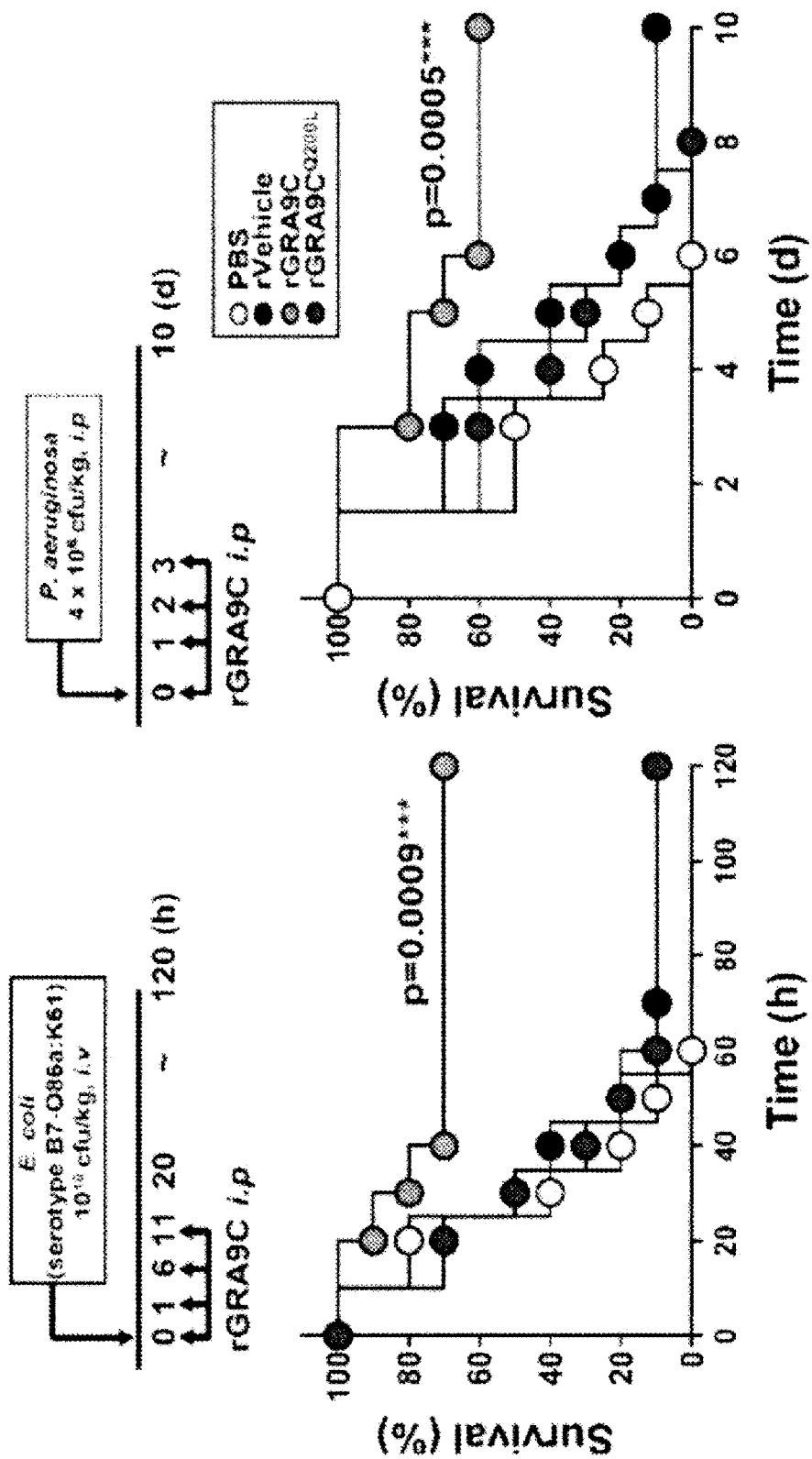
Figure 7B:
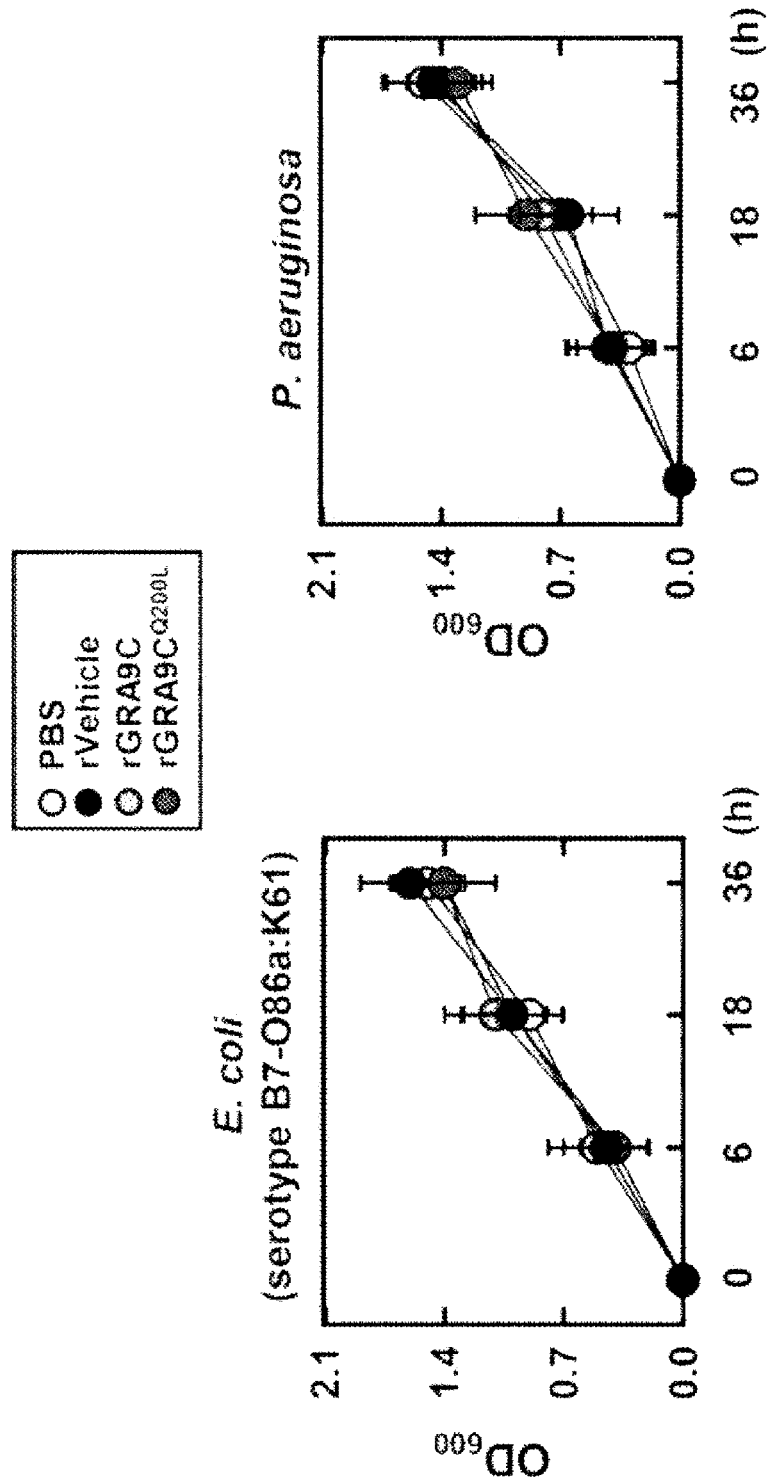
Figure 7C:
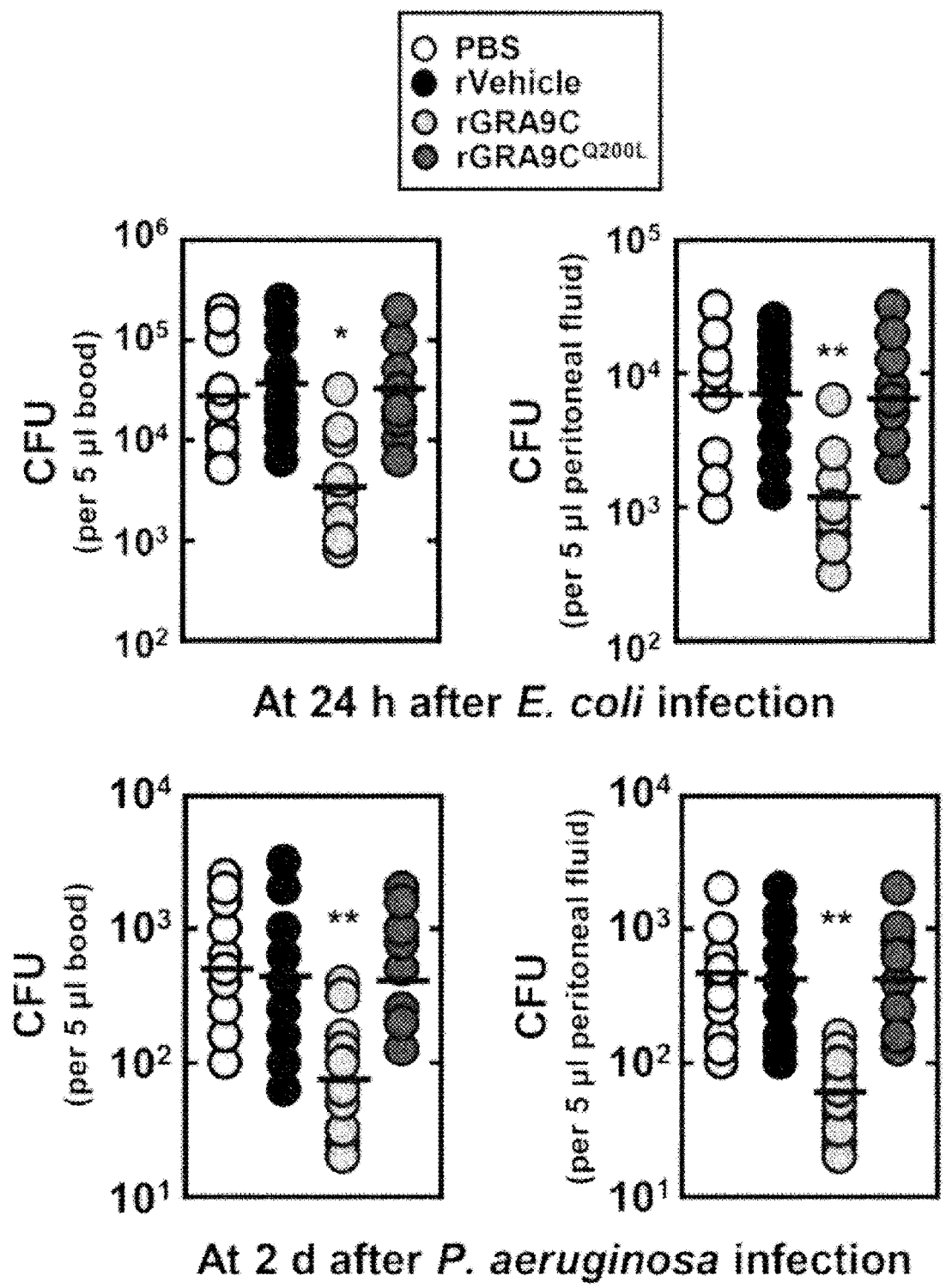
Figure 7D:
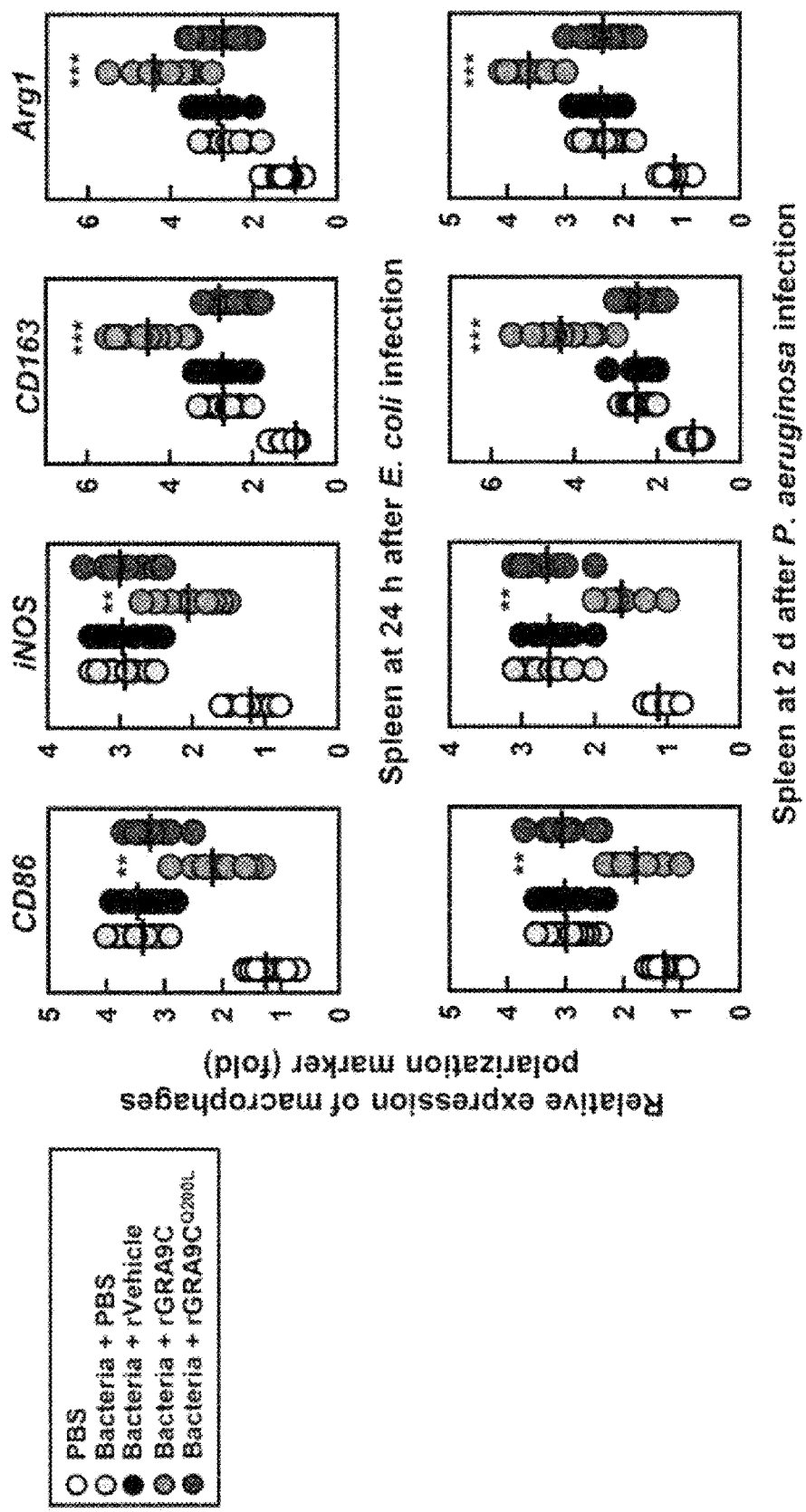

In order to evaluate the effect of GRA9C in bacterial sepsis, the present inventors intravenously or intraperitoneally infected mice with *E. coli* or *P. aeruginosa*, respectively, and administered rGRA9C or a mutant thereof according to the method shown in FIG. 7A. As shown in FIG. 7A, the results indicate that the survival rate of the mouse group administered with rGRA9C was significantly improved by about 60% compared to that of the control group (PBS or rVehicle) or the group administered with rGRA9C$^{Q200L}$. Further, as shown in FIG. 7B, the results of verifying the sterilization effect by rGRA9C indicate that the sterilization effect by rGRA9C did not appear in the LB medium, demonstrating that rGRA9C must interact with NLRP3 for its antibacterial function. In contrast, as shown in FIG. 7C, it was confirmed that formation of bacterial colonization in blood and peritoneal fluid of mice infected with *E. coli* or *P. aeruginosa* was significantly reduced by administration of rGRA9C. Further, consistent with FIG. 6F, FIG. 7D shows that macrophage polarization from M1 to M2 was increased by rGRA9C administration in mice infected with *E. coli* or *P. aeruginosa*, whereas polarization was not induced by rGRA9C$^{Q200L}$ administration.

Summarizing the above results, it can be seen that rGRA9C increases anti-inflammatory and antibacterial effects by interacting with NLRP3 in CLP-induced sepsis and bacterial sepsis model mice.

It may be easily understood by those of ordinary skill in the art to which the present invention pertains that the description of the present invention is for illustration, and it can be easily modified into other specific forms without changing the technical spirit or essential features of the present invention. Therefore, it should be understood that the embodiments described above are illustrative and not restrictive in all respects.

What is claimed is:

1. A method for treating an inflammatory disease, the method comprising a step of administering to an individual a composition including *Toxoplasma gondii* GRA9 protein as an active ingredient.

2. The method of claim 1, wherein the inflammatory disease is sepsis.

3. The method of claim 1, wherein the GRA9 protein is a C-terminal region corresponding to positions 195 to 288 in an amino acid sequence of the GRA9 protein represented by SEQ ID NO: 1.

4. The method of claim 1, wherein the GRAS protein inhibits formation of NLRP3 (NLR family pyrin domain containing 3) inflammasome by interacting with NLRP3 in mitochondria of macrophages.

5. The method of claim 1, wherein the composition reduces NLRP3-mediated inflammation.

6. The method of claim 1, wherein the composition enhances an anti-inflammatory and antibacterial effect through an increase in polarization and phagocytosis to M2 macrophages.

* * * * *

SEQUENCE LISTING

<160> NUMBER OF SEQ ID NOS: 12

<210> SEQ ID NO 1
<211> LENGTH: 318
<212> TYPE: PRT
<213> ORGANISM: Toxoplasma gondii

<400> SEQUENCE: 1

```
Met Arg Ser Leu Lys Ser Ile Val Val Pro Leu Ser Ala Ala Leu Val
1               5                   10                  15

Ala Ala Ala Glu Leu Asp Leu Phe Leu Gly Glu Ser Gly Val Tyr Leu
            20                  25                  30

Phe Gly Lys Ala Ser Glu Ser Asp Val Ala Leu Lys Val Pro Glu Asp
        35                  40                  45

Pro Val Pro Glu Glu Pro Arg Arg Glu Pro Glu Lys His Val Asp Leu
    50                  55                  60

Phe Gly Glu Asp Trp Lys Gln Phe Gly Gly Ser Gly Phe Gly Asp Phe
65                  70                  75                  80

Ser Lys Val Glu Phe Glu Asn Leu Phe Ser Gln Val His Glu Met Met
                85                  90                  95

Arg Arg Leu Met Gly Arg Gly Val Asp Gly Phe Gly Pro Ser Leu Leu
            100                 105                 110

Gly Asp Ser Pro Gly Phe His Phe Pro Arg Leu Arg Ala Leu Gln Pro
        115                 120                 125

Lys Thr Lys Leu Glu Lys Thr Gly Thr Cys Gln Tyr Val Val Thr Trp
    130                 135                 140

Ala Pro Glu Val Thr Ala Glu Asn Val Arg Val Ile Leu His Leu Gln
145                 150                 155                 160

Arg Arg Gln Val Glu Val Gln Tyr Arg Ala Ala Thr Arg Arg Asp Glu
                165                 170                 175

Lys Thr Glu Gly Gly Glu Ser His Ser Met Ser Lys Glu Gln Ser Ser
            180                 185                 190

Gln Leu Met Ser Val Asp Pro Gln Cys Ile Met Thr Arg Glu Val Val
        195                 200                 205

Ala Gln Lys Leu Ala Gly Trp Thr Asp Asn Thr His Thr Ala Thr Ala
    210                 215                 220

Gly Thr Pro Lys Lys Leu Leu Ile Ser Phe Pro Ser Pro Asp His Ile
```

```
                225                 230                 235                 240
Lys Glu Met Val Lys Glu Gly Tyr Leu Pro Asp Asn Ala Leu Glu Arg
                    245                 250                 255

Val Leu Ala Gly Asp Phe Glu Gly Phe Ser Arg Thr Gln Met Cys Leu
                260                 265                 270

Val Ser Gly Arg Asn Arg Thr Glu Cys Ala Phe Ala Glu Gly Gln Glu
            275                 280                 285

Val Glu Leu Glu Glu Lys Pro Leu Pro Ser Asp Ser Ser Pro Val Thr
        290                 295                 300

Ser Val Glu Leu Pro Arg Leu Ser Gln Glu Asp Arg Gly Leu
305                 310                 315

<210> SEQ ID NO 2
<211> LENGTH: 957
<212> TYPE: DNA
<213> ORGANISM: Toxoplasma gondii

<400> SEQUENCE: 2
atgcggtcac tcaagtcaat cgtcgtgccc ctctcggcag cgttggtcgc agcggcggaa      60
ctcgaccttt cctcggtga atcgggagtc tacttattcg ggaaagcgtc tgagtccgac     120
gtcgctctga aggttccaga ggatccggtt ccggaggaac cgcgccgtga acccgagaag     180
cacgttgacc tcttcggcga agactggaaa cagttcggcg gttccggatt cggagatttc     240
tcgaaggtgg agttcgagaa tctttttttcg caagtgcatg aaatgatgag acgccttatg     300
ggacgaggtg tggatggatt tggcccgtct cttctcggcg actctcccgg tttccacttc     360
ccccgcctca gagcgttgca accgaaaacg aagctcgaga aaactggcac gtgccagtac     420
gtggttactt gggcgccgga ggtgacggcg gagaacgttc gtgtgattct gcacttgcag     480
aggcgccagg ttgaggttca gtaccgcgca gctactcgcc gtgatgagaa gacggagggc     540
ggcgagagcc acagcatgtc gaaggagcag tcttctcagc tgatgtctgt ggacccgcaa     600
tgcatcatga cacgagaagt tgtcgcacag aaacttgctg gctggacaga caacactcac     660
accgcaacag cggggacgcc gaaaaagctc ctcatttcgt ttccgtctcc ggatcacatc     720
aaggaaatgg tcaaggaggg gtatctgcca gacaacgcgc tggaacgcgt tcttgcgggc     780
gattttgagg gattctcccg gacccagatg tgcctggtgt ccggcagaaa ccgaacggag     840
tgtgcgttcg cagagggcca agaggtcgaa ctcgaggaga gccgcttcc ctcggattcc     900 agccctgtga cgtccgtcga actgccccga ctctcgcagg aagaccgagg actctga       957

<210> SEQ ID NO 3
<211> LENGTH: 20
<212> TYPE: DNA
<213> ORGANISM: Artificial Sequence
<220> FEATURE:
<223> OTHER INFORMATION: mCD86_Forward

<400> SEQUENCE: 3
gcacgtctaa gcaaggtcac                                                  20

<210> SEQ ID NO 4
<211> LENGTH: 20
<212> TYPE: DNA
<213> ORGANISM: Artificial Sequence
<220> FEATURE:
<223> OTHER INFORMATION: mCD86_Reverse

<400> SEQUENCE: 4
```
catatgccac acaccatccg                                              20

<210> SEQ ID NO 5
<211> LENGTH: 20
<212> TYPE: DNA
<213> ORGANISM: Artificial Sequence
<220> FEATURE:
<223> OTHER INFORMATION: miNOS_Forward

<400> SEQUENCE: 5
ccccgctact actccatcag                                              20

<210> SEQ ID NO 6
<211> LENGTH: 20
<212> TYPE: DNA
<213> ORGANISM: Artificial Sequence
<220> FEATURE:
<223> OTHER INFORMATION: miNOS_Reverse

<400> SEQUENCE: 6
ccactgacac ttcgcacaaa                                              20

<210> SEQ ID NO 7
<211> LENGTH: 20
<212> TYPE: DNA
<213> ORGANISM: Artificial Sequence
<220> FEATURE:
<223> OTHER INFORMATION: mCD163_Forward

<400> SEQUENCE: 7
tgtgaccatg ctgaggatgt                                              20

<210> SEQ ID NO 8
<211> LENGTH: 20
<212> TYPE: DNA
<213> ORGANISM: Artificial Sequence
<220> FEATURE:
<223> OTHER INFORMATION: mCD163_Reverse

<400> SEQUENCE: 8
ctcgaccaat ggcactgatg                                              20

<210> SEQ ID NO 9
<211> LENGTH: 20
<212> TYPE: DNA
<213> ORGANISM: Artificial Sequence
<220> FEATURE:
<223> OTHER INFORMATION: mArg1_Forward

<400> SEQUENCE: 9
ctgagctttg atgtcgacgg                                              20

<210> SEQ ID NO 10
<211> LENGTH: 20
<212> TYPE: DNA
<213> ORGANISM: Artificial Sequence
<220> FEATURE:
<223> OTHER INFORMATION: mArg1_Reverse

<400> SEQUENCE: 10
tcctctgctg tcttcccaag                                              20

<210> SEQ ID NO 11
<211> LENGTH: 18
<212> TYPE: DNA
<213> ORGANISM: Artificial Sequence -continued

```
<220> FEATURE:
<223> OTHER INFORMATION: mb-Actin_Forward

<400> SEQUENCE: 11
aagtgtgacg ttgacatc                                                18

<210> SEQ ID NO 12
<211> LENGTH: 20
<212> TYPE: DNA
<213> ORGANISM: Artificial Sequence
<220> FEATURE:
<223> OTHER INFORMATION: mb-Actin_Reverse

<400> SEQUENCE: 12
gatccacatc tgctggaagg                                              20
```